US010919947B2

(12) United States Patent
Kwon et al.

(10) Patent No.: US 10,919,947 B2
(45) Date of Patent: *Feb. 16, 2021

(54) PHARMACEUTICAL COMPOSITION CONTAINING, AS ACTIVE INGREDIENT, FUSION PROTEIN IN WHICH TUMOR-PENETRATING PEPTIDE AND ANTI-ANGIOGENESIS AGENT ARE FUSED, FOR PREVENTING AND TREATING CANCER OR ANGIOGENESIS-RELATED DISEASES

(71) Applicant: IL DONG PHARMACEUTICAL CO., LTD., Seoul (KR)

(72) Inventors: Hyuk-Sang Kwon, Seoul (KR);
Jong-Hee Ko, Gyeonggi-do (KR);
Young-Min Lee, Incheon (KR);
Hyei-Yoon Jung, Seoul (KR);
Seok-Woo Yang, Gyeonggi-do (KR);
Jae-Hoon Kang, Seoul (KR);
Yong-Sung Kim, Gyeonggi-do (KR)

(73) Assignee: IL DONG PHARMACEUTICAL CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,086

(22) Filed: Mar. 1, 2018

(65) Prior Publication Data

US 2018/0237484 A1 Aug. 23, 2018

Related U.S. Application Data

(63) Continuation of application No. PCT/KR2016/009801, filed on Sep. 1, 2016.

(30) Foreign Application Priority Data

Sep. 1, 2015 (KR) .................. 10-2015-0123878

(51) Int. Cl.
| | |
|---|---|
| A61K 38/16 | (2006.01) |
| C07K 16/22 | (2006.01) |
| C07K 19/00 | (2006.01) |
| C07K 14/49 | (2006.01) |
| A61K 38/17 | (2006.01) |
| A61K 39/395 | (2006.01) |
| A61K 38/10 | (2006.01) |
| A61P 35/04 | (2006.01) |
| A61P 35/00 | (2006.01) |
| A61K 38/18 | (2006.01) |
| A61K 39/00 | (2006.01) |

(52) U.S. Cl.
CPC .............. *C07K 14/49* (2013.01); *A61K 38/10* (2013.01); *A61K 38/16* (2013.01); *A61K 38/17* (2013.01); *A61K 38/1866* (2013.01); *A61K 39/395* (2013.01); *A61K 39/3955* (2013.01); *A61P 35/00* (2018.01); *A61P 35/04* (2018.01); *C07K 16/22* (2013.01); *C07K 19/00* (2013.01); *A61K 2039/505* (2013.01); *C07K 2317/24* (2013.01); *C07K 2319/30* (2013.01)

(58) Field of Classification Search
CPC combination set(s) only.
See application file for complete search history.

(56) References Cited

U.S. PATENT DOCUMENTS 9,975,933 B2 * 5/2018 Kim .................. C07K 14/4703
2013/0315907 A1 11/2013 Papadopoulos et al.

FOREIGN PATENT DOCUMENTS

| EP | 3000825 A1 | 3/2016 |
|---|---|---|
| EP | 3275895 A1 | 1/2018 |
| KR | 20120048563 A | 5/2012 |
| KR | 101551299 B1 | 9/2015 |
| WO | 2005056764 A2 | 6/2005 |
| WO | 2008149143 A2 | 12/2008 |
| WO | 2008149147 A2 | 12/2008 |
| WO | 2011023130 A1 | 3/2011 |
| WO | 2013096868 A2 | 6/2013 |
| WO | 2014189303 A1 | 11/2014 |
| WO | WO 2014/189303 * 11/2014 |
| WO | 2016153276 A1 | 9/2016 |

OTHER PUBLICATIONS

Guo et al (Biochemistry, 2013, 52:7551-7558).*
Shin et al (Mol. Cancer Ther., 2014, 13:651-661; published online Jan. 16, 2014).*
Wang et al (PLoS One, Feb. 27, 2015;10(2):e0119723, internet pp. 1-17).*
Izumi et al (Nature, 2002, 416:279-280).*
Lange et al (Cancer Letters, 2011, 308:54-61).*
Sugahara, K et al., Coadministration of a Tumor-Penetrating Peptide Enhances the Efficacy of Cancer Drugs, Science, May 21, 2010, pp. 1031-1035, vol. 328, Issue 5981, American Association for the Advancement of Science, Washington DC.
Rudge, J S et al., VEGF Trap complex formation measures production rates of VEGF, providing a biomarker for predicting efficacious angiogenic blockade, Proceedings National Academy of Sciences PNAS, Nov. 20, 2007, pp. 18363-18370, vol. 104, Issue 47, National Academy of Sciences, Washington DC.

(Continued)

*Primary Examiner* — Laura B Goddard
(74) *Attorney, Agent, or Firm* — Levenfeld Pearlstein, LLC

(57) ABSTRACT

The present invention relates to a pharmaceutical composition containing, as an active ingredient, a fusion protein in which a tissue-penetrating peptide and an anti-vascular endothelial cell growth factor (anti-VEGF) agent are fused, for treating cancer or angiogenesis-related diseases. More specifically, the present invention relates to a use of the fusion protein for treating cancer or angiogenesis-related diseases, wherein the fusion protein improves the tissue penetrability of an anti-vascular endothelial cell growth factor agent and exerts a cancer targeting effect, thereby producing an excellent angiogenesis inhibiting effect and exhibiting a therapeutic effect on cancer showing resistance or unresponsiveness to the anti-VEGF agent.

10 Claims, 11 Drawing Sheets
(9 of 11 Drawing Sheet(s) Filed in Color)
Specification includes a Sequence Listing.

(56) References Cited

OTHER PUBLICATIONS

Shin, Tae-Hwan et al., Enhancement of the Tumor Penetration of Monoclonal Antibody by Fusion of a Neuropilin-Targeting Peptide Improves the Antitumor Efficacy, Molecular Cancer Therapeutics, Jan. 16, 2014, pp. 651-662, vol. 13 Issue 3, American Association for Cancer Research.

Kim, Ye-Jin et al., Immunoglobulin Fc-fused, neuropilin-1-specific peptide shows efficient tumor tissue penetration and inhibits tumor growth via anti-angiogenesis, Journal of Controlled Release, Oct. 28, 2015, pp. 56-68, vol. 216, Elsevier.

Johnson, Leslie N. et al., Cell penetrating peptide POD mediates delivery of recombinant proteins to retina, cornea and skin, Vision Research, Mar. 31, 2010, pp. 686-697, vol. 50 Issue 7, Elsevier.

Wang, Yong et al., Avastin Exhibits Therapeutic Effects on Collagen-Induced Arthritis in Rat Model, Inflammation, 2013, pp. 1460-1467, vol. 36 Issue 6, SpringerLink.

Aghajanian, Carol et al., Phase II Trial of Bevacizumab in Recurrent or Persistent Endometrial Cancer: A Gynecologic Oncology Group Study, Journal of Clinical Oncology, Jun. 1, 2011, pp. 2259-2265, vol. 29 No. 16, American Society of Clinical Oncology.

Wang, Wei-Ming et al., Epidermal Growth Factor Receptor Inhibition Reduces Angiogenesis via Hypoxia-Inducible Factor-1a and Notch1 in Head Neck Squamous Cell Carcinoma, Plos One, 2015, pp. 1-17, vol. 10 No. 2, Plos One.

Kaneko, Takehiko et al., Pharmacological and clinical profile of Cetuximab Injection (Erbitux®), Folia Pharmacologica Japonica, 2009, pp. 341-348, vol. 133 Issue 6, The Japanese Pharmacological Society.

Heskamp, Sandra et al., Abstract 866: Cetuximab treatment reduces VEGF expression and targeting of radiolabeled bevacizumab in breast cancer xenografts, Cancer Research, Apr. 2013, p. 866, vol. 73 Issue 8, American Association for Cancer Research.

\* cited by examiner

PHARMACEUTICAL COMPOSITION CONTAINING, AS ACTIVE INGREDIENT, FUSION PROTEIN IN WHICH TUMOR-PENETRATING PEPTIDE AND ANTI-ANGIOGENESIS AGENT ARE FUSED, FOR PREVENTING AND TREATING CANCER OR ANGIOGENESIS-RELATED DISEASES

TECHNICAL FIELD

The present invention relates to a pharmaceutical composition comprising, as an active ingredient, a fusion protein formed by fusion of a tumor-penetrating peptide and an anti-angiogenic agent. More specifically, the present invention relates to a use of a fusion protein for treating cancer or an angiogenesis-related disease, wherein the fusion protein has an excellent angiogenesis inhibitory effect by improving the tumor penetration of an anti-angiogenic agent and exerting the cancer targeting effect and can exhibit a therapeutic effect even on cancers showing resistance or unresponsiveness to the anti-angiogenic agent by enhancing the efficacy of the anti-angiogenic agent.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are Ajou University Industry-Academic Cooperation Foundation and Il Dong Pharmaceutical Co., LTD.

BACKGROUND ART

This application claims priority from and the benefit of Korean Patent Application No. 10-2015-0123878 filed on Sep. 1, 2015, which is incorporated herein by reference in its entity.

Angiogenesis refers to a process by which new capillaries are formed from pre-existing micro-vessels. Angiogenesis is a normal physiological action, and is known to play an important role in development, wound healing, and female reproductive cycles. In addition, there are several diseases caused by failure of self-regulation of angiogenesis and abnormal growth of blood vessels. For example, abnormally excessive angiogenesis is known to play a decisive role in cancer growth and metastasis and such diseases as diabetic retinopathy, age-related macular degeneration, rheumatoid arthritis, endometriosis, psoriasis, and chronic inflammation. On the contrary, insufficient angiogenesis is a cause of coronary artery disease, stroke, myocardial infarction, ulcer, or delayed wound healing.

Among these diseases, cancer refers to a disease in which cells constituting the body divide irregularly by the action of a certain carcinogenic factor and thus the cells per se are out of a bodily control, resulting in haphazard proliferation. Moreover, the cells invade the surrounding tissues and make distant metastasis to other organs through blood vessels, lymphatic vessels, and the like causing disorders. The neglect of such a state is fatal, and thus the state is called malignant tumor or malignant neoplasm, while such cells are called cancer cells or malignant cells.

There are various therapies according to the type of cancer, while surgery, chemotherapy inducing apoptosis, radiation therapy, cancer cell targeted therapy, immunotherapy, high-temperature therapy, stem cell transplantation, photodynamic therapy and the like are generally used. Targeted therapies have recently been often carried out in order to minimize adverse effects due to the disruption of normal cells and to increase the efficacy of drugs, while the types thereof include a signaling blocker for inhibiting cancer-specific growth, an angiogenesis inhibitor for blocking the supply of oxygen and nutrients to cancer cells, an apoptosis inducer, an immunity enhancer, and the like.

Angiogenesis, which is a process of forming new blood vessels from existing blood vessels, is one of the processes that are necessary for genesis and development of blood vessels, division and growth of normal cells and tissues, and division and growth of cancer cells.

Vascular endothelial growth factor (VEGF) is one of the several growth factors involved in angiogenesis, while the role of VEGF-A among the factors is known to be important. The anti-VEGF monoclonal antibody, bevacizumab (Avastin), which specifically inhibits VEGF-A to suppress angiogenesis, was approved as a primary or secondary medicine for metastatic colon cancer in combination with 5-fluorouracil from FDA and EMA in 2004 and 2005, respectively. Afterwards, bevacizumab (Avastin) was also approved, following hundreds of clinical trials, as a medicine for treating various cancers, such as metastatic renal cancer, metastatic non-small cell carcinoma, progressive glioblastoma, and metastatic breast cancer.

Anti-VEGF agents, such as Avastin, can target cancer accompanied by active angiogenesis. However, side effects of the anti-VEGF agents are dose-dependent in such organs as the kidney and stomach since the agents affect not only cancer but also other organs with high VEGF levels.

Besides VEGF-A, other growth factors, such as fibroblast growth factor (FGF), notch ligand/receptor system, placenta growth factor (PlGF), and platelet-derived growth factor-BB (PDGF-BB), are involved in signaling mechanisms for angiogenesis. Thus even though VEGF-A is blocked by anti-VEGF agents, such as Avastin, a compensation through other mechanisms is possible. Therefore, it is assumed that many patients are unresponsive to anti-VEGF agents, such as Avastin, or have resistance thereto due to repeated administration of Avastin, resulting in no apparent effect.

Since anti-VEGF agents, such as Avastin, possess potent anticancer activity by blocking the VEGF-A-mediated signaling to inhibit angiogenesis, they may be used as an effective agent that can be, alone or in a combinatory therapy, applied to various carcinomas including intractable metastatic cancers. Nevertheless, the anti-VEGF agents have resistances and side effects due to the mechanisms of action and dose thereof, so the anti-VEGF agents show lower clinical effects than expected and are used restrictively. Therefore, there is a need to develop novel agents capable of overcoming such disadvantages of anti-VEGF agents, such as Avastin and increasing efficacy thereof.

DETAILED DESCRIPTION OF THE INVENTION

Technical Problem

The present inventors found that a fusion protein, in which a tumor-penetrating peptide (TPP) targeting a neuropilin receptor (NRP) is fused to an anti-angiogenic agent, can increase tumor penetration of the anti-angiogenic agent, improve patient convenience and reduce dose-dependent side effects since its cancer targeting effect is exerted by TPP to reduce its high dose, and overcome a resistance derived from the change of perivascular microenvironment due to the continuous use of the anti-angiogenic agent, and then completed the present invention.

Therefore, an aspect of the present invention is to provide a pharmaceutical composition for treating cancer or an angiogenesis-related disease, the pharmaceutical composition comprising, as an active ingredient, a fusion protein obtained by fusion of a tumor-penetrating peptide and an anti-angiogenic agent.

An aspect of the present invention is to provide a pharmaceutical composition for treating cancer or an angiogenesis-related disease, the pharmaceutical composition consisting of, as an active ingredient, a fusion protein obtained by fusion of a tumor-penetrating peptide and an anti-angiogenic agent.

An aspect of the present invention is to provide a pharmaceutical composition for treating cancer or an angiogenesis-related disease, the pharmaceutical composition consisting essentially of, as an active ingredient, a fusion protein obtained by fusion of a tumor-penetrating peptide and an anti-angiogenic agent.

Another aspect of the present invention is to provide a pharmaceutical composition for inhibiting cancer metastasis, the pharmaceutical composition comprising, as an active ingredient, a fusion protein formed by fusion of a tumor-penetrating peptide and an anti-angiogenic agent.

Another aspect of the present invention is to provide a pharmaceutical composition for inhibiting cancer metastasis, the pharmaceutical composition consisting of, as an active ingredient, a fusion protein formed by fusion of a tumor-penetrating peptide and an anti-angiogenic agent.

Another aspect of the present invention is to provide a pharmaceutical composition for inhibiting cancer metastasis, the pharmaceutical composition consisting essentially of, as an active ingredient, a fusion protein formed by fusion of a tumor-penetrating peptide and an anti-angiogenic agent.

Still another aspect of the present invention is to provide a use of a fusion protein for preparing an agent for treating cancer or an angiogenesis-related disease, the fusion protein being formed by fusion of a tumor-penetrating peptide and an anti-angiogenic agent.

Another aspect of the present invention is to provide a method for treating cancer or an angiogenesis-related disease in a subject in need thereof, the method comprising administering an effective amount of a composition to a subject in need thereof, wherein the composition comprises, as an active ingredient, a fusion protein formed by fusion of a tumor-penetrating peptide and an anti-angiogenic agent.

Another aspect of the present invention is to provide a method for treating cancer or an angiogenesis-related disease in a subject in need thereof, the method comprising administering an effective amount of a composition to a subject in need thereof, wherein the composition consists of, as an active ingredient, a fusion protein formed by fusion of a tumor-penetrating peptide and an anti-angiogenic agent.

Another aspect of the present invention is to provide a method for treating cancer or an angiogenesis-related disease in a subject in need thereof, the method comprising administering an effective amount of a composition to a subject in need thereof, wherein the composition consists essentially of, as an active ingredient, a fusion protein formed by fusion of a tumor-penetrating peptide and an anti-angiogenic agent.

Another aspect of the present invention is to provide a use of a fusion protein for preparing an agent for inhibiting cancer metastasis, the fusion protein being formed by fusion of a tumor-penetrating peptide and an anti-angiogenic agent.

Another aspect of the present invention is to provide a method for inhibiting metastasis in a subject in need thereof, the method comprising administering an effective amount of a composition to a subject in need thereof, the composition comprising, as an active ingredient, a fusion protein formed by fusion of a tumor-penetrating peptide and an anti-angiogenic agent.

Another aspect of the present invention is to provide a method for inhibiting metastasis in a subject in need thereof, the method comprising administering an effective amount of a composition to a subject in need thereof, wherein the composition consists of, as an active ingredient, a fusion protein formed by fusion of a tumor-penetrating peptide and an anti-angiogenic agent.

Another aspect of the present invention is to provide a method for inhibiting metastasis in a subject in need thereof, the method comprising administering an effective amount of a composition to a subject in need thereof, wherein the composition consists essentially of, as an active ingredient, a fusion protein formed by fusion of a tumor-penetrating peptide and an anti-angiogenic agent.

Technical Solution

In accordance with an aspect of the present invention, there is provided a pharmaceutical composition for treating cancer or an angiogenesis-related disease, the pharmaceutical composition comprising, as an active ingredient, a fusion protein obtained by fusion of a tumor-penetrating peptide and an anti-angiogenic agent.

In accordance with an aspect of the present invention, there is provided a pharmaceutical composition for treating cancer or an angiogenesis-related disease, the pharmaceutical composition consisting of, as an active ingredient, a fusion protein obtained by fusion of a tumor-penetrating peptide and an anti-angiogenic agent.

In accordance with an aspect of the present invention, there is provided a pharmaceutical composition for treating cancer or an angiogenesis-related disease, the pharmaceutical composition consisting essentially of, as an active ingredient, a fusion protein obtained by fusion of a tumor-penetrating peptide and an anti-angiogenic agent.

In accordance with another aspect of the present invention, there is provided a pharmaceutical composition for inhibiting cancer metastasis, the pharmaceutical composition comprising, as an active ingredient, a fusion protein formed by fusion of a tumor-penetrating peptide and an anti-angiogenic agent.

In accordance with another aspect of the present invention, there is provided a pharmaceutical composition for inhibiting cancer metastasis, the pharmaceutical composition consisting of, as an active ingredient, a fusion protein formed by fusion of a tumor-penetrating peptide and an anti-angiogenic agent.

In accordance with another aspect of the present invention, there is provided a pharmaceutical composition for inhibiting cancer metastasis, the pharmaceutical composition consisting essentially of, as an active ingredient, a fusion protein formed by fusion of a tumor-penetrating peptide and an anti-angiogenic agent.

In accordance with another aspect of the present invention, there is provided a use of a fusion protein for preparing an agent for treating cancer or an angiogenesis-related disease, the fusion protein being formed by fusion of a tumor-penetrating peptide and an anti-angiogenic agent.

In accordance with another aspect of the present invention, there is provided a method for treating cancer or an angiogenesis-related disease in a subject in need thereof, the method comprising administering an effective amount of a composition to a subject in need thereof, wherein the composition comprises, as an active ingredient, a fusion protein formed by fusion of a tumor-penetrating peptide and an anti-angiogenic agent.

In accordance with another aspect of the present invention, there is provided a method for treating cancer or an angiogenesis-related disease in a subject in need thereof, the method comprising administering an effective amount of a composition to a subject in need thereof, wherein the composition consists of, as an active ingredient, a fusion protein formed by fusion of a tumor-penetrating peptide and an anti-angiogenic agent.

In accordance with another aspect of the present invention, there is provided a method for treating cancer or an angiogenesis-related disease in a subject in need thereof, the method comprising administering an effective amount of a composition to a subject in need thereof, wherein the composition consists essentially of, as an active ingredient, a fusion protein formed by fusion of a tumor-penetrating peptide and an anti-angiogenic agent.

In accordance with another aspect of the present invention, there is provided a use of a fusion protein for preparing an agent for inhibiting cancer metastasis, the fusion protein being formed by fusion of a tumor-penetrating peptide and an anti-angiogenic agent.

In accordance with another aspect of the present invention, there is provided a method for inhibiting metastasis in a subject in need thereof, the method comprising administering an effective amount of a composition to a subject in need thereof, wherein the composition comprises, as an active ingredient, a fusion protein formed by fusion of a tumor-penetrating peptide and an anti-angiogenic agent.

In accordance with another aspect of the present invention, there is provided a method for inhibiting metastasis in a subject in need thereof, the method comprising administering an effective amount of a composition to a subject in need thereof, wherein the composition consists of, as an active ingredient, a fusion protein formed by fusion of a tumor-penetrating peptide and an anti-angiogenic agent.

In accordance with another aspect of the present invention, there is provided a method for inhibiting metastasis in a subject in need thereof, the method comprising administering an effective amount of a composition to a subject in need thereof, wherein the composition consists essentially of, as an active ingredient, a fusion protein formed by fusion of a tumor-penetrating peptide and an anti-angiogenic agent.

Hereinafter, the present invention will be described in detail.

The present invention provides a pharmaceutical composition for treating cancer or an angiogenesis-related disease, the pharmaceutical composition comprising, as an active ingredient, a fusion protein obtained by fusion of a tumor-penetrating peptide and an anti-angiogenic agent.

Furthermore, the present invention provides a pharmaceutical composition for treating cancer or an angiogenesis-related disease, the pharmaceutical composition consisting of, as an active ingredient, a fusion protein obtained by fusion of a tumor-penetrating peptide and an anti-angiogenic agent.

Furthermore, the present invention provides a pharmaceutical composition for treating cancer or an angiogenesis-related disease, the pharmaceutical composition consisting essentially of, as an active ingredient, a fusion protein obtained by fusion of a tumor-penetrating peptide and an anti-angiogenic agent.

Vascular endothelial growth factor-A (VEGF-A) is well known to induce extravasation. This is also called a vascular permeability factor. This action is known to be induced by its binding to a vascular endothelial growth factor receptor (VEGFR2), while interestingly, mutation experiments on vascular endothelial growth factor-A showed that the vascular permeability of vascular endothelial growth factor-A was increased even though vascular endothelial growth factor-A failed to bind to the vascular endothelial growth factor receptor. This suggested that there is another receptor for vascular endothelial growth factor-A (Stacker et al., 1999).

Neuropilin was first found in the *Xenopus* nervous system by Takagi et al., (1987) and Fujisawa et al., (1989). Neuropilin is a transmembrane glycoprotein, while there are two types of neuropilins, NRP1 and NRP2. Neuropilin acts as a co-receptor for VEGF receptors (VEGFRs) by binding to VEGF family ligand. It was revealed through the change in binding affinity between VEGF165 and VEGFR2 by NRP1 that NRP1 binds to various VEGF ligands by acting as a co-receptor for VEGFR1, VEGFR2, and VEGFR3, thereby enhancing the binding strength between a ligand and a receptor (Soker et al., 1998). On the other hand, NRP2 contributes to lymphangiogenesis and cell adhesion by acting as a co-receptor for VEGFR2 and VEGFR3. In addition, while acting as a co-receptor for the Plexin family receptors, NRP1/NRP2 (NRP1/2) binds to secreted class 3 semaphorin ligands (Sema3A, Sema3B, Sema3C, Sema3D, Sema3E, Sema3F, and Sema3G).

NRP1 acts as a co-receptor with VEGFR-2 to increase cell migration and angiogenesis in endothelial cells and to be involved in vascular reconstruction procedure in which pericytes cover blood vessels, and thus NRP1 is a main factor in the vascular development. In addition, NRP1 increases the expression of vascular endothelial (VE)-cadherin and epithelium-specific cell adhesion molecule (E-cadherin) to maintain adherent junction among cells. Especially, NRP1 is highly expressed in various cancer cell lines including the lung, breast, prostate, pancreas, and large intestine cancer, while it is known that in advanced colorectal carcinoma patients, the high expression of NRP1 results in a high possibility of cancer metastasis to lymph nodes or the liver and leads to a short survival rate. As such, the relationship between NRP1 and cancer metastasis has also been clinically verified.

As used herein, the term "tumor penetrating" refers to having any one characteristic among specifically recognizing NRP-overexpressing tissues and being accumulated therein, increasing the cell gap between vascular endothelial cells to promote the extravasation of drugs, and adjusting the gap between corneal cells, which are a tissue serving as a barrier against water-soluble molecules, to promote the distribution of a drug in the tissue.

Angiogenesis requires a series of various and complicated processes, such as simple growth of vascular endothelial cells, invasion of endothelial cells into basement membranes, migration and differentiation thereof, and capillary formation. There have been reported many promoters and inhibitors to control the angiogenic process. In addition, the activation of histolytic enzymes and the like are needed for angiogenesis, while such a series of processes is very similar to the invasion procedure of cancer cells.

The most well-known angiogenesis promoting factor is vascular endothelial growth factor (VEGF). VEGF is 32-44 kDa in size, secreted in almost all cells, and highly correlated with tumor invasion (Takahashi et al., 1995). VEGF was earlier known to be a vascular permeability factor, and showed a 50,000 times more potent extravasation effect than histamine (Senger et al., 1983). The characteristics of such extravasation characteristics move proteins in the blood out of blood vessels to help the formation of new blood vessels.

In recent years, angiopoietin proteins have been newly isolated and purified, and are known to play a key role in the formation of angiogenic structures. Angiopoietin (ANG) proteins are classified into Ang-1 and Ang-2, which bind to Tie-2 receptor specifically present in endothelial cells. Ang-1 is involved in the differentiation and stabilization of endothelial cells, whereas Ang-2 binds to Tie-2 receptor to inhibit the binding of Ang-1 binding, resulting in non-stabilization and vascular regression of endothelial cells. For angiogenesis in cancer tissues, cancer cells first select an existing blood vessel, and are subjected to vascular co-option and vascular regression, which are mediated by Ang-2 (Holash et al., 1999).

Angiogenesis is known to be promoted by activating a series of receptors using various ligands including, in addition to VEGF and ANG above, placenta growth factor (PlGF), fibroblast growth factor (FGF), platelet-derived growth factor (PDGF), hepatocyte growth factor (HGF), transforming growth factor (TGF), insulin-like growth factor (IGF), ephrin, interleukin, and bone morphogenetic protein (BMP).

As used herein, the "anti-angiogenesis" includes molecules that interfere with interactions between angiogenesis-related molecules and natural receptors, for example, molecules that bind to VEGF or VEGF receptors to prevent or inhibit interactions between VEGF and VEGF receptors. VEGF antagonists include anti-VEGF antibodies, anti-VEGF receptor antibodies, and VEGF receptor-based chimeric molecules. The "anti-angiogenesis" also includes molecules that bind to PDGF, PlGF, FGF, TGF, ANG, HGF, IGF, ephrin A, interleukin, BMP, and receptors thereof to prevent or inhibit interactions therebetween. The antagonists thereto include anti-PDGF, anti-PlGF, anti-FGF, anti-TGF, anti-ANG, anti-HGF, anti-IGF, anti-ephrin A, anti-interleukin, and anti-BMP antibodies, and antagonistic antibodies to respective receptors, and receptor-based chimeric molecules.

As used herein, the term "fusion" refers to integrating two molecules with the same or different functions or structures, and may be a fusion by any physical, chemical, or biological method whereby a tumor-penetrating peptide may bind to an anti-angiogenic agent. The fusion may be accomplished preferably by a linker peptide, and such a linker peptide may bind to, for example, C-terminus of Fc fragment in an antibody.

Meanwhile, anti-angiogenic agents are effective drugs that can be applied alone or in a combinatory therapy to various cancers including intractable metastatic cancers since the anti-angiogenic agents have high anticancer activity by blocking angiogenesis-related signaling to inhibit angiogenesis. Nevertheless, the anti-angiogenic agents have resistances and side effects due to the mechanisms of action and dose thereof, so the anti-angiogenic agents show lower clinical efficacy than expected and are used restrictively. It is known that the anti-VEGF agent, Avastin (chemical name: bevacizumab), which is one of the most representative drug among anti-angiogenic agents, is not a cancer-specific targeted drug, unlike other antibody medicines, and therefore, Avastin needs to be administered at a high dose in order to exert efficacy thereof and may be distributed in not only cancer tissues but also other tissues with a high level of VEGF, resulting in adverse side effects.

The fusion protein of the present invention targets NRPs that are abundantly distributed in cancer since a tumor-penetrating peptide targeting NRP is fused to an anti-angiogenic agent, so that the fusion protein can increase cancer-specific effects of the anti-angiogenic agent to reduce the dose thereof, thereby increasing patient convenience and reducing dose-dependent side effects.

In addition, NRP1 binds with VEGF-A as well as other growth factors, such as VEGF-B, -C, -D, -E and PDGF, while acting as a co-receptor together with VEGFR-1 or -2, so that the binding of NRP1 and the growth factors is inhibited through the tumor-penetrating peptide fused in the fusion protein of the present invention, thereby increasing the angiogenesis inhibitory effect of the anti-angiogenic agent.

The present invention provides a pharmaceutical composition characterized in which the cancer or angiogenesis-related disease is resistant or non-responsive to the anti-angiogenic agent.

The term "resistant" or "non-responsive" refers to a property showing no therapeutic effect at a drug concentration at which a therapeutic effect is generally exhibited.

Besides VEGF-A, other growth factors, such as FGF, notch ligand/receptor system, P1GF, and PDGF-BB, are involved in signaling mechanisms for angiogenesis, and thus even though one signal is blocked, angiogenesis may continuously occur as a compensation action through other mechanisms. It is therefore assumed that many patients are unresponsive to anti-angiogenic agents or have resistance thereto due to repeated administration, resulting in no apparent therapeutic effect.

More specifically, an example may be the use of an anti-VEGF agent among the anti-angiogenic agents. In angiogenesis, vascular growth occurs through cell division and growth at a high VEGF concentration. Thereafter, as the VEGF concentration decreases, the PDGF concentration is increased, and thus vascular normalization or reconstruction occurs. The normalization procedure encompasses, together with a decrease in number and size of immature blood vessels, a process of reducing the vascular pressure by the interstitial fluid due to pericyte coverage of blood vessels. In cases where the VEGF concentration is lowered by the administration of an anti-VEGF agent, such as Avastin, the vascular pericyte coverage is increased through normalization, thereby lowering the penetration of a drug into cancer tissues. It has been reported that the co-administration of Avastin and docetaxel to non-small cell lung cancer patients actually reduced the penetration of the drug into cancer. These results indicate that the co-administration of an anti-VEGF agent, such as Avastin, and another drug has a limitation and causes resistance to the anti-VEGF agent.

Meanwhile, the fusion protein of the present invention has an anti-angiogenic agent and a tumor-penetrating peptide fused thereto, the tumor-penetrating peptide being capable of directly binding to and acting on NRP, while NRP is involved in vascular reconstruction through pericyte association. Thus the tissue-penetrating peptide in the fusion protein of the present invention inhibits NRP, thereby directly suppressing the angiogenic development and overcoming the resistance derived from the change of perivascular microenvironment due to the continuous use of the anti-angiogenic agent.

In addition, since NRP1 regulates the expression of VE-cadherin and E-cadherin involved in maintaining the intercellular junction, the fusion protein of the present invention loosens the intercellular gap by inhibiting NRP1, thereby increasing the penetration ability of a co-administered drug, such as an existing antibody medicine, and immune cells into the cancer mass, thus increasing efficacy of the drug.

According to an example of the present invention, the present inventors evaluated various physiological activities by fabricating an Avastin-A22p fusion protein in which a tissue-penetrating peptide A22p is fused to the C-terminus of an anti-VEGF agent, Avastin, and an Avastin-TPP11 fusion protein in which TPP11 is fused to the same. Specifically, the fusion proteins according to the present invention showed (i) excellent binding ability to NRP1 and VEGF (Example 2), (ii) significantly enhanced cancer-targeting ability and tissue penetration ability compared with wild type Avastin (Example 3), (iii) a significantly reduced pericyte coverage, which is assumed to be a resistance mechanism of an anti-VEGF agent (Example 4), and (iv) excellent antitumor activity even in tumor animal models (Example 5).

The reason why the fusion protein of the present invention shows excellent physiological activities as above is considered that the anti-VEGF agent and the tumor-penetrating peptide exhibit a synergistic effect by simultaneously acting on VEGF and NRP1, respectively.

The pharmaceutical composition according to the present invention can be formulated into a suitable form containing the fusion protein alone or together with a pharmaceutically acceptable carrier, and may further contain an excipient or a diluent. The term "pharmaceutically acceptable" composition refers to a non-toxic composition that is physiologically acceptable, and does not cause an allergic response, such as gastrointestinal disorder or vertigo, or similar responses, when administered to humans.

Examples of the pharmaceutically acceptable carrier may further include a carrier for oral administration or a carrier for parenteral administration. The carrier for oral administration may include lactose, starch, cellulose derivatives, magnesium stearate, stearic acid, and the like. In addition, the carrier for oral administration may include various drug delivery materials used for oral administration of peptide preparations. Also, the carrier for parenteral administration may include water, suitable oil, saline, aqueous glucose, and glycol, and may further include a stabilizer and a preservative. Suitable examples of the stabilizer include an antioxidant, such as sodium hydrogen sulfite, sodium sulfite, or ascorbic acid. Suitable examples of the preservative include benzalkonium chloride, methyl- or propyl-paraben, and chlorobutanol. The pharmaceutical composition of the present invention may further contain, in addition to the above ingredients, a lubricant, a wetting agent, a sweetening agent, a flavoring agent, an emulsifier, a suspending agent, and the like. Other pharmaceutically acceptable carriers and preparations may be referred to in the literature (Remington's Pharmaceutical Sciences, 19th ed., Mack Publishing Company, Easton, Pa., 1995).

The composition of the present invention may be administered to mammals including humans by any method. For example, the composition of the present invention may be administered orally or parenterally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration.

The pharmaceutical composition of the present invention may be formulated as an agent for oral administration or parental administration according to the route of administration as described above.

For an agent for oral administration, the composition of the present invention may be formulated in forms of a powder, granules, a tablet, a pill, a sugar-coated tablet, a capsule, a liquid, a gel, a syrup, a slurry, and a suspension, by the methods known in the art. For example, the tablet or sugar-coated tablet for an oral administration may be obtained by mixing an active ingredient with a solid excipient, pulverizing the mixture, adding a suitable adjuvant thereto, and then processing the mixture into a granule mixture. Suitable examples of the excipient may include: sugars including lactose, dextrose, sucrose, sorbitol, mannitol, xylitol, erythritol, and maltitol; starches including corn starch, wheat starch, rice starch, and potato starch; celluloses including cellulose, methyl cellulose, sodium carboxy methyl cellulose, and hydroxypropyl methyl cellulose; and fillers, such as gelatin and polyvinyl pyrrolidone. In some cases, cross-linked polyvinyl pyrrolidone, agar, alginic acid, or sodium alginate may be added as a disintegrant. Furthermore, the pharmaceutical composition of the present invention may further contain an anti-coagulant, a lubricant, a wetting agent, a favoring agent, an emulsifier, and a preservative.

For agents for parental administration, the composition of the present invention may be formulated in forms of an injection, a cream, a lotion, an external ointment, an oil, a moisturizer, a gel, an aerosol, and a nasal inhaler, by the methods known in the art. These dosage forms are disclosed in the literature, which is a formulary generally known in all pharmaceutical chemistries (Remington's Pharmaceutical Science, 19th ed., Mack Publishing Company, East on, Pa., 1995).

A total effective amount of the composition of the present invention may be administered to a patient in a single dose, or may be administered in multiple doses over a long period by a fractionated treatment protocol. In the pharmaceutical composition of the present invention, the content of the active ingredient may vary depending on the severity of disease. A total dose of the pharmaceutical composition of the present invention may be preferably about 0.01 µg to 10,000 mg, and more preferably 0.1 µg to 1,000 mg relative to 1 kg of patient body weight per day. As for the dose of the pharmaceutical composition of the present invention, an effective dose to a patient is determined according to various factors, such as the method for formulation, route of administration, number of times of treatment, patient's age, body weight, health condition, and sex, severity of disease, food intake, and excretion rate. Thus considering these factors, a person skilled in the art could determine an appropriate effective amount of the composition of the present invention. The pharmaceutical composition according to the present invention is not particularly limited to the dosage form, route of administration, and administration method thereof.

The present invention provides a pharmaceutical composition characterized in that the anti-angiogenic agent is selected from the group consisting of:

an anti-vascular endothelial growth factor (anti-VEGF) agent, an anti-platelet-derived growth factor (anti-PDGF) agent, an anti-placenta growth factor (anti-PIGF) agent, an anti-fibroblast growth factor (anti-FGF) agent, an anti-transforming growth factor (anti-TGF) agent, an anti-angiopoietin (anti-ANG) agent, an anti-hepatocyte growth factor (anti-HGF) agent, an anti-insulin-like growth factor (anti-IGF) agent, an anti-Activin receptor-like kinase 1 (anti- ALK1) agent, an anti-ephrin A agent, an anti-interleukin agent, an anti-bone morphogenetic protein (anti-BMP) agent;

antagonistic antibodies to receptors for VEGF, PDGF, PIGF, FGF, TGF, ANG, HGF, IGF, ALK1, ephrin A, or interleukin; and chimeric molecules based on the receptors.

In the present invention, the anti-vascular endothelial growth factor (anti-VEGF) agent may be selected from the group consisting of bevacizumab, ranibizumab, r84 (PLoS One. 2010 Aug. 6; 5(8)), aflibercept, conbercept, CTO1 (WO2005056764A2), DOM15-10-11 (WO2008149147A2), DOM15-26-593 (WO2008149143A2), PRS-050 (PLoS One. 2013 Dec. 13; 8(12)), CT-322 (BMC Cancer 2008, 8:352), ESBA903 (Eur J Pharm Biopharm. 2015 Mar. 14. pii: 50939-6411(15)00089-2), EPI-0030 (WO2011023130A1), and an antibody-drug conjugate in which anti-VEGF antibody and a drug are fused. The anti-VEGF agent encompasses biosimilars and variants thereof. More preferably, the anti-VEGF agent may be ranibizumab, bevacizumab, aflibercept, or conbercept, but is not limited thereto.

The term "biosimilar" refers to a copy medical product that is verified to have equivalence in light of quality, efficacy, and safety by mimicking an off-patent original biological medical product that has been already developed or marketed by using biotechnology, such as genetic recombination and cell culture technology.

while retaining the core physiological activity of the anti-vascular endothelial growth factor agent, the variant include all similar sequences that contain one or more variations at amino acid positions that do not affect such activity. That is, the variant may be a functional variant that is at least 80%, more preferably at least 85%, still more preferably at least 90%, and the most preferably at least 95% identical to amino acid sequences of the above listed anti-vascular endothelial growth factor agents.

As used herein, the term "antagonistic antibodies to receptors" refer to antibodies that may suppress at least one biological activity of receptors for VEGF, PDGF, PIGF, FGF, TGF, ANG, HGF, IGF, ALK1, ephrin A, and interleukin. These antibodies may show functions of inhibiting molecular biological signaling for angiogenesis by inhibiting the binding of the receptors to the ligands. The antibody may include a polyclonal antibody, a monoclonal antibody, a chimeric antibody, a humanized antibody, Fv-fragment, Fab-fragment, F(ab')$_2$-fragment, and scFv fragment, and the antibody includes a form of the whole antibody and a functional fragment of the antibody molecule.

As used herein, the term "angiogenesis-related disease" refers to a disease caused by vasculogenesis in which capillaries extend in the form that vascular endothelial cells sprout from an existing blood vessel and invade tissues. Unlimited examples of the disease may include rheumatoid arthritis, psoriasis, inflammation, endometriosis, and hemangioma.

In the present invention, the cancer may be selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, perianal cancer, esophagial cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, colorectal cancer, endometrial or uterine cancer, salivary gland tumor, kidney cancer, liver cancer, prostate cancer, vulvar cancer, thyroid cancer, and head or neck cancer, but is not limited thereto.

In addition, the present invention provides a pharmaceutical composition characteized in that the tumor-penetrating peptide binds to both neuropilin 1 (NRP1) and neuropilin 2 (NRP2) or specifically binds only to neuropilin 1.

In the present invention, the tumor-penetrating peptide binding to both neuropilin 1 and neuropilin 2 comprises an amino acid sequence selected from the group consisting of SEQ ID NO: 1 to SEQ ID NO: 4, while the tumor-penetrating peptide specifically binding only to neuropilin 1 comprises an amino acid sequence selected from the group consisting of SEQ ID NO: 5 to SEQ ID NO: 7.

The tissue-penetrating peptide represented by an amino acid sequence selected from SEQ ID NO: 1 to SEQ ID NO:4 can bind to both neuropilins 1 and 2, and is designed based on the facts that the amino acid sequence of a binding region of VEGF$_{165}$ ligand, which binds to b1b2 domain of neuropilin, and the length of the amino acid sequence are analyzed, and the nucleotide sequences of the furin C-terminus sequences of semaphorin 3A and semaphorin 3F, which are known to bind to neuropilin, are analyzed, and thus the sequences of the C-termini thereof are similar to each other.

The tissue-penetrating peptide represented by an amino acid sequence selected from the group consisting of SEQ ID NO: 5 to SEQ ID NO: 7 specifically binds only to neuropilin 1 without binding to neuropilin2. The present inventors isolated and purified peptides, which were derived by designing peptide libraries fused to the C-terminus of the heavy chain constant region (Fc), expressing the peptide libraries on yeast cell surfaces to construct Fc-fused peptide libraries, and then selecting clones selectively binding to b1 domain of neuropilin 1. Meanwhile, in order to isolate the peptides, which are specific to neuropilin 1 and bind to neuropilin 1 at high affinity, from the Fc-peptide libraries, peptides were fabricated by carrying out selection using b1b2 domain protein of neuropilin 1 and, at the same time, carrying out selection using, as a competitor therefor, b1b2 domain protein of neuropilin 2.

The amino acid sequences of SEQ ID NO: 1 to SE ID NO: 7 are as follows:

| | | |
|---|---|---|
| TPP#1 | (SEQ ID NO: 1) | HTPGNSNKWKHLQENKKGRNRR |
| TPP#2 | (SEQ ID NO: 2) | HTPGNSNKWKHLQENKKGRPRR |
| TPP#3 | (SEQ ID NO: 3) | REAPGAPRSPEPQDQKKPRNRR |
| TPP#4 | (SEQ ID NO: 4) | REAPGAPRSPEPQDQKKPRPRR |
| TPP#5 | (SEQ ID NO: 5) | HTPGNSNQFVLTSTRPPR |
| TPP#6 | (SEQ ID NO: 6) | HTPGIATRTPR |
| TPP#7 | (SEQ ID NO: 7) | HTPGNSKPTRTPRR |

In the present invention, the fusion protein may be characterized in that the tissue-penetrating peptide and the anti-VEGF agent are fused via a linker. The linker peptide may be composed of 1 to 100 amino acids, preferably 4 to 20 amino acids, more preferably 4 to 15 amino acids. In addition, the linker peptide may be composed of glycine (G), serine (S), or alanine (A), and the sequence of the linker peptide may be preferably an amino acid sequence of (GA)$_n$or (GGGGS)$_m$ (provided that n and m each are independently an integer of 1 to 20), and more preferably an amino acid sequence of GAGA or (GGGGS)$_3$. In an embodiment of the present invention, the amino acid sequence represented by SEQ ID NO: 8 (GGGGSGGGGSGGGGS) was used as the linker.

According to a preferable embodiment of the present invention, the fusion protein, which is a fusion of Avastin and a tissue-penetrating peptide, may be a fusion protein having an amino acid sequence of SEQ ID NO: 9 or 10 as a heavy chain and an amino acid sequence of SEQ ID NO: 11 as a light chain. In addition, the fusion protein, which is a fusion of an Avastin variant and a tissue-penetrating peptide, may be a fusion protein having the amino acid sequence of SEQ ID NO: 12 as a heavy chain and the amino acid sequence of SEQ ID NO: 11 as a light chain.

The present invention provides a pharmaceutical composition for inhibiting cancer metastasis, the pharmaceutical composition comprising, as an active ingredient, a fusion protein formed by fusion of a tumor-penetrating peptide and an anti-angiogenic agent.

Furthermore, the present invention provides a pharmaceutical composition for inhibiting cancer metastasis, the pharmaceutical composition consisting of, as an active ingredient, a fusion protein formed by fusion of a tumor-penetrating peptide and an anti-angiogenic agent.

Furthermore, the present invention provides a pharmaceutical composition for inhibiting cancer metastasis, the pharmaceutical composition consisting essentially of, as an active ingredient, a fusion protein formed by fusion of a tumor-penetrating peptide and an anti-angiogenic agent.

Cancer metastasis refers to the formation of new cancer from the dissemination of cancer cells from primary cancer to other organs. Since metastasis is a major life-threatening condition in various cancer patients, the prevention or control of the metastasis is an important goal in cancer research. While surgery, chemotherapy, or radiotherapy is effective in the early diagnosis of cancer without metastasis, the effects of these therapies are reduced when there is metastasis at the time of diagnosis. In addition, metastasis is often confirmed during or after therapy, while metastasis has not been confirmed at the time of diagnosis.

Metastasis is composed of a series of stages: invasion, intravasation, arrest, extravasation, colonization and the like. Through this procedure, cancer cells disseminate from the primary organ, and finally, form cancer in other organs. The invasion as its first stage is an initiation stage of metastasis and encompasses a change in interaction between cancer cells or between cancer cells and extracellular matrix, disintegration of surrounding tissues, and migration of cancer cells into tissues, and the like.

In an Example of the present invention, it was confirmed that the treatment of tumor cell lines exhibiting resistance to Avastin with the fusion protein (Avastin-A22p) according to the present invention significantly inhibited the migration of tumor cells. The reason is considered to be that the fusion protein according to the present invention inhibits signaling by other growth factors as well as VEGF-A, and thus also exhibits an excellent metastasis inhibitory effect on tumor cells having resistance to Avastin.

Meanwhile, it is known that the binding of PDGF to a PDGF receptor in cancer cells increases the phosphorylation of p130cas protein to promote the migration and invasion of cancer cells. However, it was confirmed that the phosphorylation of p130cas protein, which had not been significantly changed by Avastin treatment, was suppressed to a phosphorylation level of a control group by Avastin-A22p treatment. That is, it can be considered that the fusion protein according to the present invention inhibits VEGF, and also inhibits PDGF-mediated signaling by binding to NRP1, thereby suppressing the migration and invasion of tumor cells by PDGF. Thus it is suggested that the fusion protein of the present invention exhibits an effective metastasis inhibitory effect even on tumor cells having resistance to an anti-VEGF agent.

Therefore, in the present invention, the cancer may be resistant or non-responsive to anti-angiogenic agents.

The present invention provides a use of a fusion protein for preparing an agent for treating cancer or an angiogenesis-related disease, the fusion protein being formed by fusion of a tumor-penetrating peptide and an anti-angiogenic agent.

The present invention provides a method for treating cancer or an angiogenesis-related disease in a subject in need thereof, the method comprising administering an effective amount of a composition to a subject in need thereof, the composition comprising, as an active ingredient, a fusion protein formed by fusion of a tumor-penetrating peptide and an anti-angiogenic agent.

Furthermore, the present invention provides a method for treating cancer or an angiogenesis-related disease in a subject in need thereof, the method comprising administering an effective amount of a composition to a subject in need thereof, the composition consisting of, as an active ingredient, a fusion protein formed by fusion of a tumor-penetrating peptide and an anti-angiogenic agent.

Furthermore the present invention provides a method for treating cancer or an angiogenesis-related disease in a subject in need thereof, the method comprising administering an effective amount of a composition to a subject in need thereof, the composition consisting essentially of, as an active ingredient, a fusion protein formed by fusion of a tumor-penetrating peptide and an anti-angiogenic agent.

The present invention provides a use of a fusion protein for preparing an agent for inhibiting cancer metastasis, the fusion protein being formed by fusion of a tumor-penetrating peptide and an anti-angiogenic agent.

The present invention provides a method for inhibiting metastasis in a subject in need thereof, the method comprising administering an effective amount of a composition to a subject in need thereof, the composition comprising, as an active ingredient, a fusion protein formed by fusion of a tumor-penetrating peptide and an anti-angiogenic agent.

Furthermore, the present invention provides a method for inhibiting metastasis in a subject in need thereof, the method comprising administering an effective amount of a composition to a subject in need thereof, the composition consisting of, as an active ingredient, a fusion protein formed by fusion of a tumor-penetrating peptide and an anti-angiogenic agent.

Furthermore, the present invention provides a method for inhibiting metastasis in a subject in need thereof, the method comprising administering an effective amount of a composition to a subject in need thereof, the composition consisting essentially of, as an active ingredient, a fusion protein formed by fusion of a tumor-penetrating peptide and an anti-angiogenic agent.

The term "effective amount" refers to the amount showing an effect of alleviating, treating, preventing, detecting, or diagnosing cancer or an angiogenesis-related disease, or an effect of inhibiting or reducing cancer metastasis. The term "subject" refers to an animal, preferably, a mammal, and especially, an animal including a human being, and may be a cell, tissue, and organ, or the like originating from an animal. The subject may be a patient in need of such effects.

As used herein, the term "treating" broadly refers to alleviating cancer or an angiogenesis-related diseases or symptoms of cancer or an angiogenesis-related disease, and may include healing, substantially preventing, or alleviating the condition of these diseases, and may include alleviating, curing, or preventing one or most of the symptoms resulting from cancer or an angiogenesis-related disease, but is not limited thereto.

As used herein, the term "comprising" is used synonymously with "comprising" or "being characterized by", and does not exclude additional ingredients or steps that are not mentioned in the compositions and methods. The term "consisting of" excludes additional elements, steps, or ingredients that are not otherwise indicated. The term "consisting essentially of" means that in view of compositions or methods, the term includes described materials or steps as well as any material or step that does not substantially affect basic characteristics thereof.

Advantageous Effects

The pharmaceutical composition comprising, as an active ingredient, a fusion protein formed by fusion of a tissue-penetrating peptide and an anti-angiogenic agent, for treating cancer or an angiogenesis-related disease can improve the tumor penetration of the anti-angiogenic agent, can exert a cancer targeting effect, thereby exhibiting excellent treatment effects with even a small dose, thus reducing side effects of the anti-angiogenic agent, and can exhibit excellent treatment effects on even cancer or an angiogenesis-related disease having resistance to the anti-angiogenic agent by binding an angiogenesis growth factor and NRP1 at the same time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 3A: Avastin, FIG. 3B: Avastin-A22p).

MODE FOR CARRYING OUT THE INVENTION

Hereinafter, the present invention will be described in detail.

The following Examples are merely for illustrating the present invention and are not intended to limit the scope of the present invention.

Figure 1:
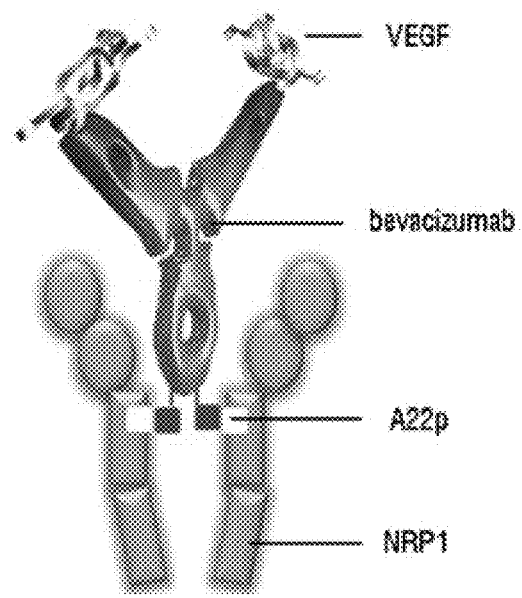
FIG. 1 is a schematic diagram of a fusion protein (Avastin-A22p) formed by fusion of a tumor-penetrating peptide and an anti-vascular endothelial growth factor.

Example 1: Fabrication of Avastin-Tissue-Penetrating Peptide (TPP) Fusion Protein For increasing efficacy and overcoming resistance with respect to an anti-VEGF agent, Avastin, the present inventors have attempted to fuse a tissue-penetrating peptide (TPP), which is capable of binding to both neuropilin 1 (NRP1) and neuropilin 2 or specifically binding only to neuropilin 1, to the C-terminus of Avastin. The amino acid sequences of TPP are shown in Table 1 below. Among the sequence listing on Table 1, TPPs having the amino acid sequences of SEQ ID NO: 1 to SEQ ID NO: 4 can bind to both neuropilins 1 and 2, while TPPs having the amino acid sequence of SEQ ID NO: 5 to SEQ ID NO: 7 can bind specifically only to neuropilin 1. A schematic diagram of a fusion protein in which TPP is fused to Avastin is shown in FIG. 1.

Avastin as used herein is a peptide having the amino acid sequence of SEQ ID NO: 13 for a heavy chain and the amino acid sequence of SEQ ID NO: 11 for a light chain, and used for the present experiment after purchase from www-.Drugbank.com.

Meanwhile, among TPPs shown in Table 1, A22p as TPP having the amino acid sequence of SEQ ID NO: 2 was obtained by modifying the C-terminus regions of $VEGF_{165}$ as an intrinsic ligand of the neuropilin and class 3 semaphorin ligands; and TPP11 was obtained by isolating and identifying a peptide derived from clones selectively binding to the b1 domain of neuropilin 1 using both the b1b2 domain protein of neuropilin 1 and the b1b2 domain protein of neuropilin 2 as competitors. Here, Avastin as a linker was fused thereto to act as a bivalent on the neuropilin receptor, so that these peptides were designed to possess a capability of tissue penetration while having a similar affinity to VEGF and Sema3A ligands.

TABLE 1

TPP sequence information

| | | |
|---|---|---|
| TPP#1 | (SEQ ID NO: 1) | HTPGNSNKWKHLQENKKGRNRR |
| TPP#2 | (SEQ ID NO: 2) | HTPGNSNKWKHLQENKKGRPRR |
| TPP#3 | (SEQ ID NO: 3) | REAPGAPRSPEPQDQKKPRNRR |
| TPP#4 | (SEQ ID NO: 4) | REAPGAPRSPEPQDQKKPRPRR |
| TPP#5 | (SEQ ID NO: 5) | HTPGNSNQFVLTSTRPPR |
| TPP#6 | (SEQ ID NO: 6) | HTPGIATRTPR |
| TPP#7 | (SEQ ID NO: 7) | HTPGNSKPTRTPRR |

Specifically, fusion proteins in which TPP (A22p) having the amino acid sequence of SEQ ID NO: 2 and TPP (TPP11) having the amino acid sequence of SEQ ID NO: 7 were fused to the C-terminus of Avastin, respectively, and cell lines producing the fusion proteins were fabricated as described below.

<1-1> Construction of Expression Vector and Cell Transfection

Selection marker DHFR genes were inserted into pcDNA3.1(−) vectors, and heavy and light chains of Avastin-A22p and Avastin-TPP11 were cloned by restriction enzymes NotI and BamHI, respectively. A plasmid encoding the protein formed by fusion of each of the constructed antibody heavy constant regions and a peptide binding to NRP1 and a plasmid encoding a light chain protein were expressed for protein in CHO DG44 cells (obtained from Prof. Chasin) using Neon™ electroporesis. In T25 flask, 3×10⁶ cells transfected with each plasmid were inoculated and incubated at 37° C. Stable cells were secured using the selection marker, and then cultured in a floating state in serum-free SFM4CHO (Hyclone) for 7 days under conditions of 100 rpm, 37° C., pH 7.2, 50% DO₂ in a bioreactor. The supernatant was separated from the cells through centrifugation, and sterilized using a 0.22-μm filter.

<1-2> Purification of Fusion Protein

The cultures of Avastin, Avastin-A22p, and Avastin-TPP11 were collected, and respective proteins thereof were purified while referring to a standard protocol. For the purification column, the protein A resin (MabselectSure resin, GE healthcare) was packed to 20 mL in the XK16/20 column (MabselectSure resin, GE healthcare), to which a linear speed of 200 cm/h was applied. 1 L of antibody was applied to the protein A column, and the column was washed with a 15-fold column volume of PBS (pH 7.4, 137 mM NaCl, 2.7 mM KCl, 10 mM Na₂HPO₄, 2 mM KH₂PO₄). The antibody was eluted with 100 mL of 0.1 M glycine buffer at pH 3.0. The proteins were collected between 10 mAU and 10 mAU in the UV absorbance at 280 nm, and 60 mL of the proteins were neutralized to pH 7.0 using 0.7 mL of 1 M Tris buffer. The antibody fractions were filtered by a 0.2 μm-filter (Milipore), and then concentrated using an amicon (30 MWCO) concentrator (Milipore) at 3,500 rpm for 10 min, followed by exchange with PBS (pH 7.4) buffer. The purified fusion protein formed by fusion of the purified antibody heavy chain constant region and the selected peptide specifically binding to NRP1 was quantified using absorbance and absorption coefficient at a corrected wavelength of 280 nm. The purified fusion protein formed by fusion of the purified antibody heavy chain constant region and the selected peptide specifically binding to NRP1 was analyzed on 10% SDS-PAGE in reduction and non-reduction conditions.

Figure 2:
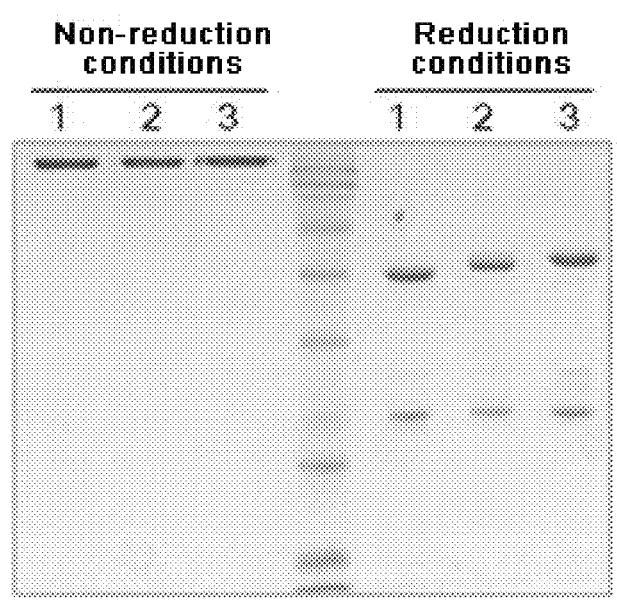
FIG. 2 shows SDS-PAGE results of confirming a fusion protein formed by fusion of a tumor-penetrating peptide and an anti-vascular endothelial growth factor (Lane 1: Avastin, Lane 2: Avastin-A22p, Lane 3: Avastin-TPP11).

The proteins were respectively purified from the cultures collected from the cell lines expressing Avastin, Avastin-A22p, and Avastin-TPP11, and separated by SDS-PAGE. FIG. 2 confirmed that Avastin-A22p and Avastin-TPP11 successfully formed antibodies, peptides were fused to Avastin in reduction conditions, and Avastin-A22p and Avastin-TPP11 were larger than Avastin in reduction conditions. In addition, it was confirmed that TPP fusion did not significantly affect antibody expression since Avastin-A22p and Avastin-TPP11 were expressed at similar levels.

In order to investigate the purity of Avastin-A22p purified protein, high performance lipid chromatography (HPLC) assay was performed. Agilent 1200 (Agilent) was used, and a size exclusion column (Biosuite 250, Waters) was used.

Specifically, a buffer solution (pH 6.2) containing 0.2 M potassium phosphate and 0.25 M potassium chloride was used as a mobile phase, and allowed to flow down at a flow rate of 0.35 ml/min for 20 min. The size of the protein was checked according to the retention time, and the purity thereof was checked according to the area and height.

Figure 3A:
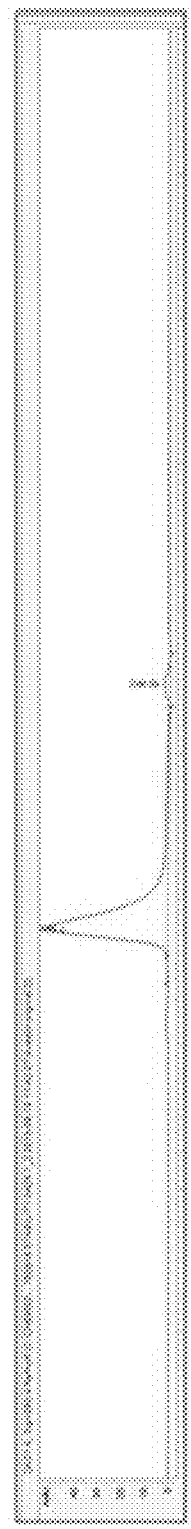
FIGS. 3A and 3B show SE-HPLC results of confirming a fusion protein (Avastin-A22p) formed by fusion a tumor-penetrating peptide and an anti-vascular endothelial growth factor.
Figure 3B:
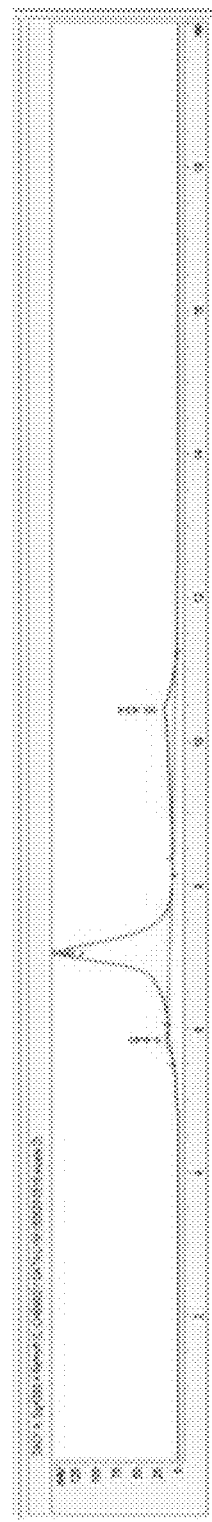

As shown in FIG. 3, the purity of purified Avastin-A22p was analyzed using SE-HPLC. It was confirmed that the purity of Avastin-A22p was 97% or higher, and was larger than Avastin.

The present inventors, hereinafter, fabricated Avastin-A22p fusion protein in which A22p as a TPP having the amino acid sequence represented by SEQ ID NO: 2 was fused to Avastin, and evaluated activity thereof.

Example 2: Binding Ability of Avastin-Tissue-Penetrating Peptide (TPP) Fusion Protein to NRP1 and VEGF In order to evaluate whether the N-terminus of the fusion protein Avastin-A22p as prepared in Example 1 may bind to VEGF in the same manner as Avastin while its C-terminus may bind to NRP1 to thus dually block the associated signaling, the binding of Avastin-A22p with NRP1 and VEGF was respectively evaluated.

The binding ability of the purified Avastin-A22p to Neuropilin 1-b1b2 domain was investigated in enzyme-linked immunosorbent assay (ELIA). Herceptin-A22p (HCT-A22p) as a positive control and Avastin (Roche co., Swiss) as a negative control were used. The target molecule Neuropilin 1-b1b2 domain (273-586) was reacted at 1 μg per well in the 96-well Maxibinding Immuno plate (SPL Life sciences., Korea) for 2 h at 37° C., and then washed with 0.1% PBST (0.1% Tween20, pH 7.4, 137 mM NaCl, 2.7 mM KCl, 10 mM Na₂HPO₄, 2 mM KH₂PO₄) for 1 min three times. After reaction with 0.1% PBST containing 5% skim milk for 1 h, the reaction product was washed with 0.1% PBST for 1 min three times. Herceptin-A22p as a positive control and Avastin (Roche co., Swiss) as a negative control were used. Avastin-A22p, as experimental groups, was diluted with 0.1% PBST to 50 nM, 25 nM, 12.5 nM, and 6.25 nM, and the solutions were then treated at 37° C. for 1 h for each different concentrations, and washed with 0.1% PBST for 1 min three times. HRP-conjugated anti-kappa light chain antibody (Horseradish peroxidase-conjugated anti-human kappa light chain mAb, SIGMA-ALDRICH Co., USA) was 100,000-fold diluted with 0.1% PBST containing 5% skim milk, followed by treatment at 37° C. for 30 min. Thereafter, the reaction product was washed with 0.1% PBST for 1 min five times. For color development, the resultant product was treated with the TMB HRP colorimetric substrate (Surmodics co., USA), followed by reaction at room temperature for 10 min, treatment with the same volume of 1 N HCl (stop buffer), and then absorbance measurement at 450 nm. The binding ability of the expressed and purified Avastin-A22p to Neuropilin 1-b1b2 domain was confirmed through the obtained ELISA results.

The binding ability of the purified Avastin-A22p to Recombinant human VEGF 165 (R&D systems co. China) was investigated in ELISA. Avastin as a positive control and HCT-A22p as a negative control were used. The target molecule Recombinant human VEGF 165 was reacted at 0.2 µg per well in the 96-well Maxibinding Immuno plate for 2 h at 37° C., and then washed with 0.1% PBST for 1 min three times. After reaction with 1% PBST containing 5% skim milk for 1 h, the reaction product was washed with 0.1% PBST for 1 min three times. Avastin as a positive control and Herceptin-A22p as a negative control were used. Avastin-A22p, as experimental groups, was diluted with 0.1% PBST to 1.5 nM, 0.75 nM, 0.35 nM, and 0.17 nM, and the solutions were then treated at 37° C. for 1 h for each different concentrations, and washed with 0.1% PBST for 1 min three times. HRP-conjugated anti-kappa light chain antibody was 100,000-fold diluted with 0.1% PBST containing 5% skim milk, followed by treatment at 37° C. for 30 min. Thereafter, the reaction product was washed with 0.1% PBST for 1 min five times. For color development, the resultant product was treated with the TMB HRP colorimetric substrate, followed by reaction at room temperature for 10 min, treatment with the same volume of 1 N HCl, and then absorbance measurement at 450 nm. The binding ability of the expressed and purified Avastin-A22p to Recombinant human VEGF 165 was confirmed through the obtained ELISA results.

Figure 4A:
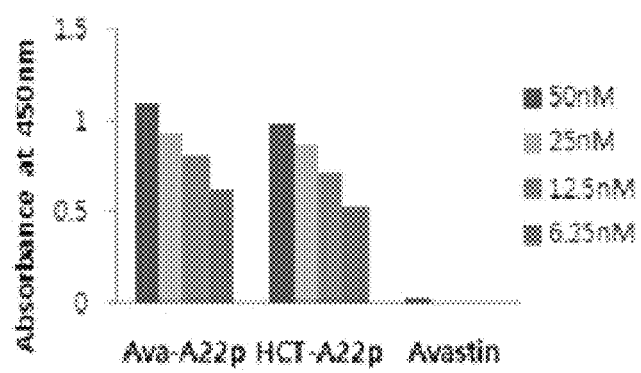
FIGS. 4A and 4B show the results of evaluating the binding strength of Avastin-A22p with NRP1 or VEGF (FIG. 4A: binding strength with NRP1, FIG. 4B: binding strength with VEGF).
Figure 4B:
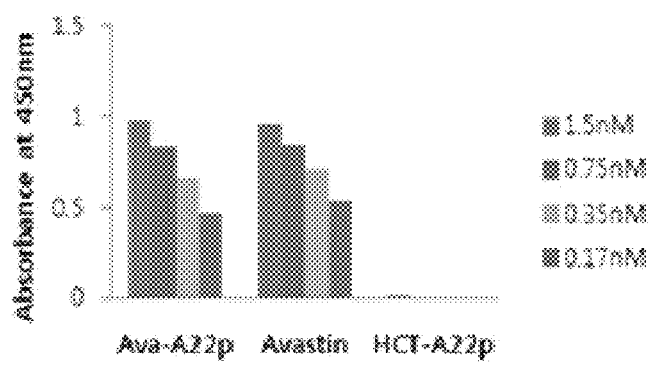

Related results are shown in FIG. 4.

As shown in FIG. 4, it was confirmed that Avastin-A22p bound to NRP1 at the same level as in HCT-A22p used as a control, and also bound to VEGF at the same level as in Avastin.

Example 3: Cancer Targeting Experiment of Avastin-A22p

It is known that Avastin is not a cancer-specific targeted drug, unlike other antibody medicines, and thus Avastin needs to be administered at a high dose for exerting efficacy and may be distributed in not only cancer tissues but also other tissues with a high level of VEGF, resulting in adverse side effects. Therefore, the use of the cancer-specific distribution of NRP1 is expected to increase the cancer targeting effect to reduce the dose, thereby increasing patient convenience and reducing dose-dependent side effects. The present inventors have attempted to evaluate whether Avastin-A22p can effectively target cancer.

In order to investigate whether Avastin-A22p is distributed better than Avastin in cancer cells by targeting NRP1 present in new blood vessels inside cancer tissues and cancer mass, when a tumor volume reached around 250 mm$^3$ after SW620 (obtained from ATCC) was transplanted in nude mice, PBS, Avastin-A22p, or Avastin was intravenously administered at 5 mg/kg, respectively, and tumors were harvested at the elapsed time of 3, 8, and 16 h, and the distribution of proteins in the cancer tissue was investigated through immunohistochemistry using fluorescence microscopes.

More specifically, the harvested tumor was sectioned to a thickness of 8 µm by a paraffin section method, and perivascular cells were stained with, as primary antibody, NG2 antibody (Cell Signaling technology, USA) and secondary antibody conjugated to Alexa (red fluorescence, Life Technologies) recognizing the NG2 antibody. In order to observe Avastin and Avastin-A22p distributed in the tissue, an antibody conjugated to Alexa®488 (green fluorescence, Life Technologies) recognizing IgG was used.

Figure 5:
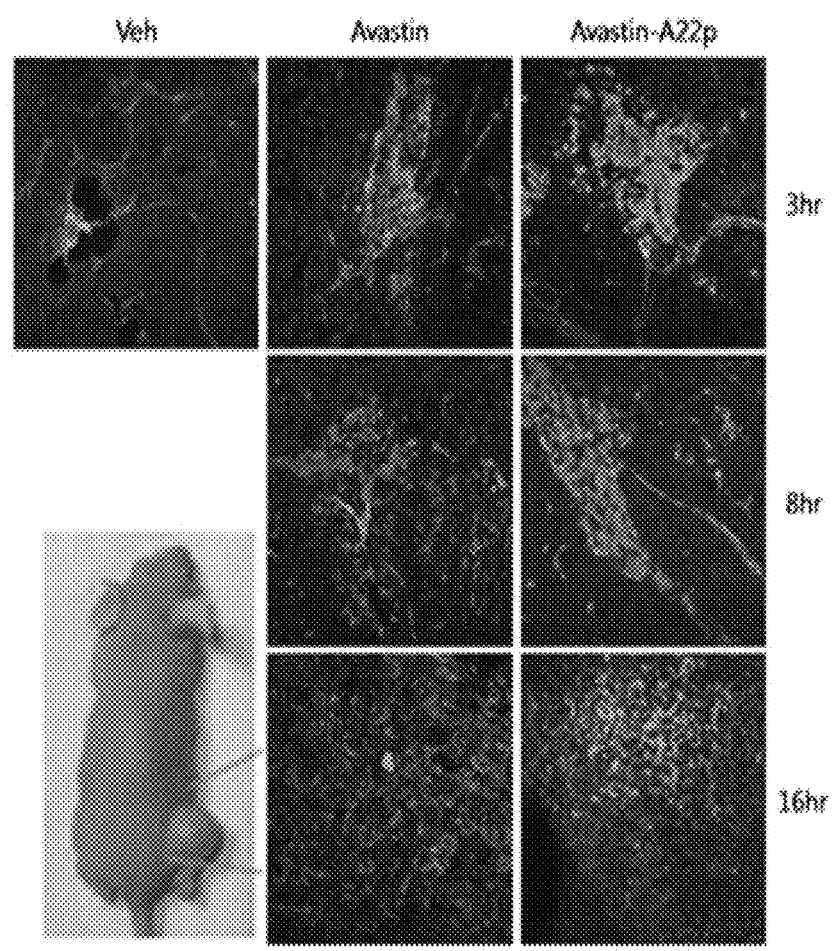
FIG. 5 shows the results of observing the distribution of proteins in cancer tissues through fluorescent microscopy at the elapsed time of 3, 8, and 16 h after the administration of Avastin and Avastin-A22p into SW620 xenograft animal models (Veh: saline-administered group).

Related results are shown in FIG. 5.

As shown in FIG. 5, it was confirmed that Avastin-A22p was higher in concentration in the cancer tissue than Avastin from 3 h after administration; as time passed, a greater amount of Avastin-A22p was also distributed in cells distant from the blood vessels; and Avastin-A22p also effectively reduced angiogenesis inside cancer mass.

From the results of the present fluorescent microscopic observation, it is suggested that Avastin-A22p is expected to have excellent cancer targeting ability and tissue penetration ability in comparison with Avastin, while Avastin-A22p, unlike Avastin, may inhibit angiogenesis more effectively by inhibiting various angiogenic factors, such as VEGF-B, VEGF-C, P1GF as well as VEGF-A. Through these results, even a low dose of Avastin-A22p can target tumor, leading to reduced side effects. Furthermore, it could be expected that Avastin-A22p arrives at not only cancer cells close to blood vessels but also cancer tissues inside the cancer mass due to high penetration ability thereof, and thus inhibits the activity of various angiogenic factors, including VEGF-A, secreted in these cells, thereby inhibiting cell division and thus enhancing anticancer activity.

In conclusion, such results have verified that Avastin-A22p may be applied to the treatment of Avastin-non-responsive cases occurring due to relatively lower dependency on VEGF-A than the other angiogenic factors.

Example 4: Effect of Avastin-A22p7 on Pericyte Coverage

In angiogenesis, vascular growth occurs through cell division and growth at a high VEGF concentration, and then as the VEGF concentration decreases, the PDGF concentration is increased, and thus vascular normalization or reconstruction occurs. The normalization encompasses, together with a decrease in number and size of immature blood vessels, a process of reducing the vascular pressure by the interstitial fluid due to pericyte coverage of blood vessels. When the concentration of VEGF is lowered by Avastin administration, blood vessels increase pericyte coverage through normalization to weaken the penetration of a drug into the cancer tissue. It has been reported that the co-administration of Avastin and docetaxel into non-small cell lung cancer patients reduced the penetration of drugs into cancer (Arjaans et al., 2013). This fact indicates that the co-administration of Avastin and another drug has limitations, and may cause resistance to Avastin.

According to the report by Fan et al., the continuous treatment of primary or metastatic colorectal cancer cell lines with Avastin for three months resulted in cell lines adapted to Avastin from both the cell lines, and these cell lines showed the same cell growth as existing cell lines, but have increased cell migration, and thus showed faster metastasis than existing cancer cells in the xenograft. VEGFR1 and NRP1 were specifically highly expressed in such Avastin adapted cell lines, which were then transformed into cells that secrete various angiogenic factors, such as VEGF-A, VEGF-B, VEGF-C, and P1GF, in larger quantities, showing resistance to Avastin (Fan et al., 2011). Therefore, it was considered that the treatment with Avastin-A22p or Avastin-TPP11 capable of binding to NRP1 to inhibit signaling of various angiogenic factors in addition to VEGF-A will effectively inhibit the growth and metastasis of cell lines showing Avastin resistance.

In addition, on the basis of the report in which when anti-NRP1 antibody and a VEGF inhibitor are co-administered, the reduction of pericyte coverage of blood vessels by the anti-NRP1 antibody may be directly related to the enhancement of anti-cancer efficacy through the control of vascular normalization and may be involved in overcoming resistance, the present inventors conducted a fluorescent microscopic comparison test of a change of pericyte coverage in cancer tissues in a xenograft model administered with Avastin and Avastin-A22p, respectively.

In order to investigate angiogenesis and vascular stabilization inhibitory ability of Avastin-A22p in mouse models, SW620 was transplanted in nude mice, which were then administered with Avastin-A22p and Avastin, respectively, and the pericyte coverage in cancer tissue was monitored by fluorescence microscopy. When the tumor volume reached around 250 mm$^3$ after SW620 cells were injected into Balb/c nude mice, PBS, Avastin, and Avastin-A22p were intravenously administered at 5 mg/kg for each mouse, respectively. After 16 h, tumors were harvested from the mice, followed by immunohistochemistry. The harvested tumor was sectioned to a thickness of 8 μm by a paraffin section method. Then vascular cells were stained with, as primary antibody, PECAM1 (Sigma) and secondary antibody conjugated to Alexa®488 recognizing PECAM1, while perivascular cells were stained with, as primary antibody, NG2 antibody and secondary antibody conjugated to Alexa®594 recognizing NG2 antibody.

Figure 6:
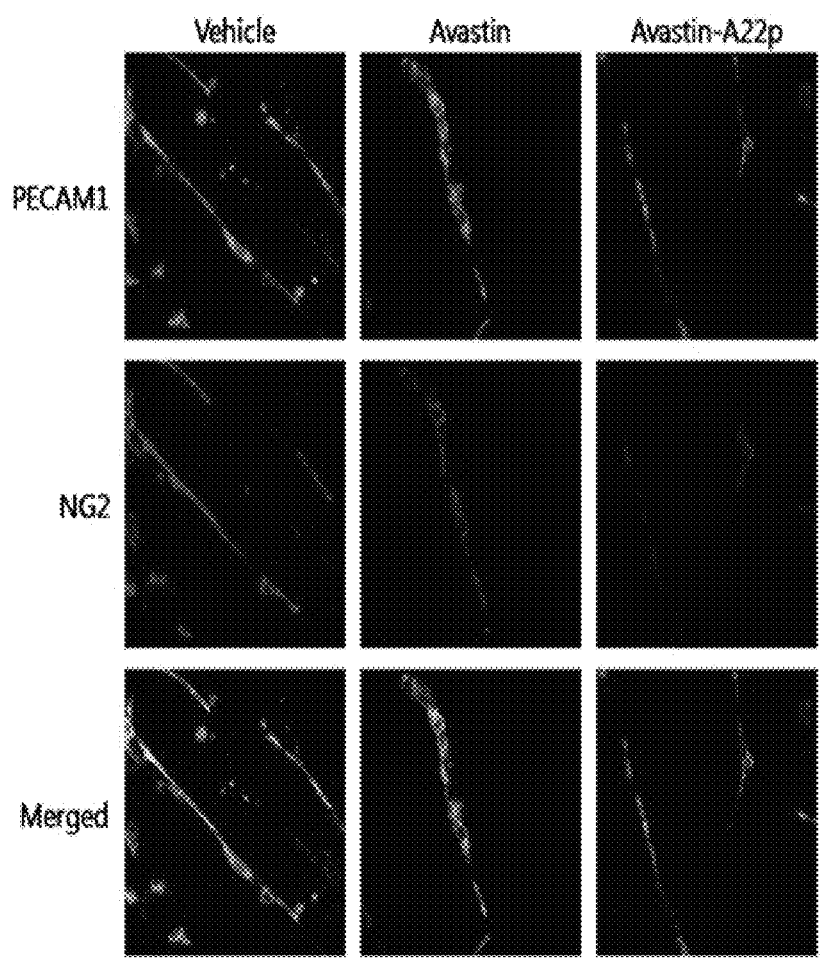
FIG. 6 shows the results of evaluating the change of pericyte coverage in cancer cells in the treatment with Avastin-A22p (PECAM1: blood vessel staining, NG2: pericyte staining).

Related results are shown in FIG. 6.

As shown in FIG. 6, it was confirmed that the pericyte coverage relative to blood vessels were distinctively lowered in Avastin-A22p administered group rather than Avastin-administered group, and thus the increase of the anticancer effect by Avastin-A22p can be expected to be involved in the pericyte coverage. These results are identical to the test results of animals co-administered with anti-NRP1 antibody developed by Genetech Inc., and Avastin. It was confirmed that the VEGF- and NRP1-inhibitory effects by Avastin-A22p were similar to those by respective independent antibodies. That is, it can be verified that Avastin-A22p is a protein in a concept of a dual specific antibody that inhibit VEGF and NRP1 at the same time.

These results may suggest that through the reduction of pericyte coverage by A22p, Avastin-A22p can increase the angiogenesis inhibitory effect and overcome the resistance occurring due to the continuous administration of Avastin.

Example 5: Evaluation of In Vivo Anticancer Efficacy of Avastin-A22p

In order to investigate anticancer efficacy of Avastin-A22p, a comparison test with Avastin was conducted on colon cancer cell line SW620 xenograft models. The SW620 cell line is a tumor cell line with 45% RGI to VEGF, and this animal experiment was conducted for the purpose of evaluating the anticancer efficacy against general tumors. It was confirmed through a pre-experiment that Avastin-A22p showed an efficacy equal to or higher than that of Avastin (results not shown), and in this experiment, SW620 cell-xenograft Balb/c-nude mice were intravenously administered with Avastin 5 mg/kg and Avastin-A22p 0.5, 1.25, 2.5 mg/kg twice a week for five weeks, respectively.

Figure 7:
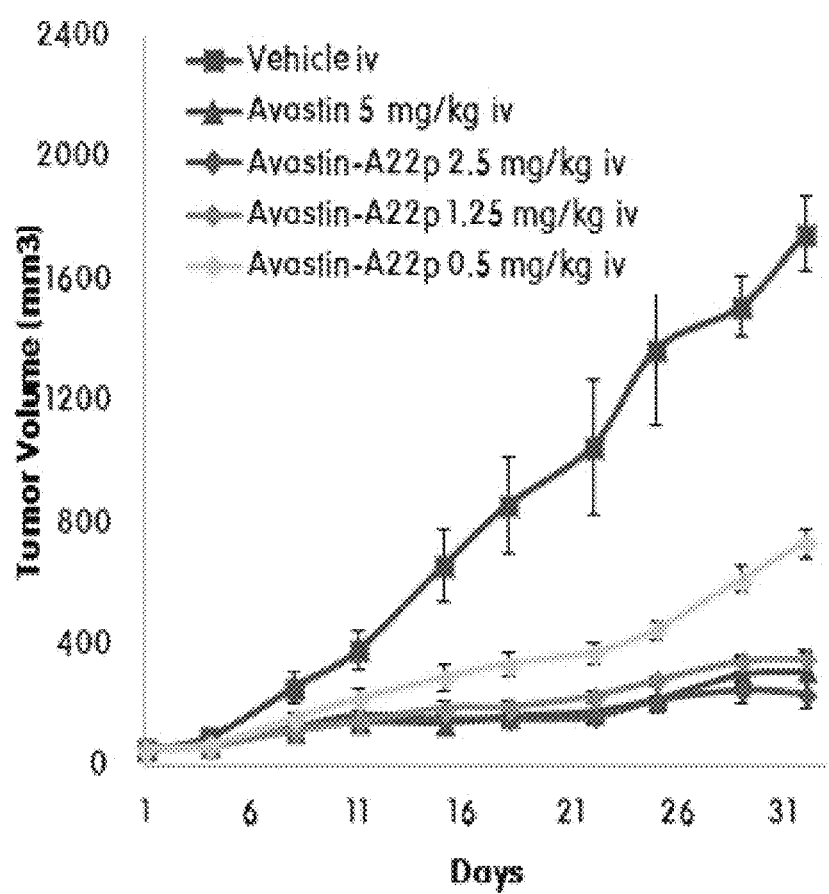
FIG. 7 shows the results of evaluating anticancer efficacy of Avastin-A22p in SW620 xenograft animal models.

Related results are shown in FIG. 7.

As shown in FIG. 7, it was confirmed that the Avastin 5 mg/kg-administered group and the Avastin-A22p 1.25 mg/kg-administered group showed a similar inhibitory effect against cancer growth. That is, it can be seen that the Avastin-A22p fusion protein can exhibit an equivalent anticancer efficacy even with one quarter of the dose of Avastin.

The fact that Avastin-A22p fusion protein may exhibit an equivalent anticancer efficacy even with one quarter of the dose of Avastin is thought to result from the blocking of NRP1 signaling by A22p, suggesting that adverse side effects may be also reduced through the reduction of dose in the clinical applications.

Example 6: Test of Confirming Resistant Cell Line Migration Inhibition by Avastin-A22p One of the causes of resistance and responsiveness to Avastin is that VEGF-A, as a target of Avastin, and other growth factors, such as FGF, notch ligand/receptor system, PlGF, and PDGF-BB are involved in signaling mechanisms. NRP1 is known to affect signaling by serving as a co-receptor together with VEGFR1, VEGFR3, C-met, and PDGFR as well as VEGFR2 binding with VEGF-A. The present inventors investigated whether A22p fused to Avastin inhibits the binding to NRP1 competitively with other angiogenic factors which bind to NRP1.

HCT116/bev cell lines (provided from L M Ellis, MD anderson), which had been obtained resistance to Avastin by continuous treatment of HCT116 cells (obtained from ATCC) with Avastin, were treated with Avastin and Avastin-A22p to investigate the migration inhibitory ability thereof, respectively. In comparison with its parent cells HCT116, HCT116/bev has higher expression levels of VEGF-A, VEGF-B, VEGF-C, and P1GF, with a better ability in cell migration and metastasis (Fan et al., 2011). Thus, if Avastin-A22p inhibits the migration of HCT116/bev cells, the possibility of Avastin-A22p to overcome resistance to Avastin and increase efficacy thereof can be confirmed. A specific test method was as follows.

HCT116 and HCT116/bev cells were each seeded at 4×10$^5$ cells/well in the 6-well plate, and incubated for 2 days. Thereafter, a cross-shaped blank was made in each well. The medium was removed, and 50 ng/ml VEGF was added and dispensed to MEM-alpha medium supplemented with 1% FBS. Avastin and Avastin-A22p each were treated to become 1 μM. The blank was photographed immediately after the drug treatment (0 h), and the same position was photographed at 2 h intervals from 48 h. The cell migration inhibitory abilities of Avastin-A22p and Avastin were compared by calculating the width of the empty blank from the photographing results through the Image J program and inversely quantifying the degree of cell migration therefrom.

Figure 8A:
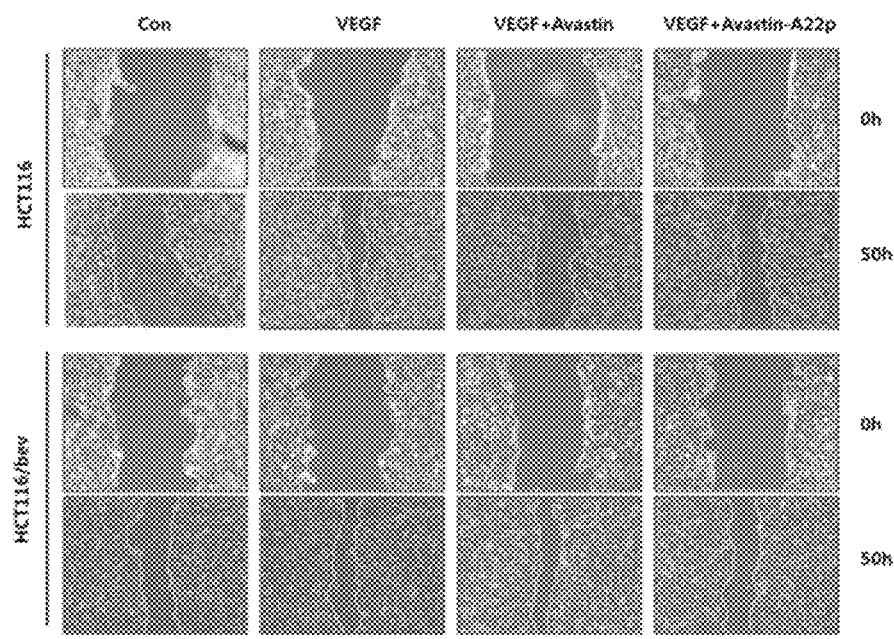
FIGS. 8A and 8B show the results of confirming the migration inhibitory effect when HCT116/bev cells showing Avastin resistance were treated with VEGF to induce migration and then treated with 1 μM Avastin or Avastin-A22p (FIG. 8A: microscopic images, FIG. 8B: Microscopic observations results quantified and plotted as a graph).
Figure 8B:
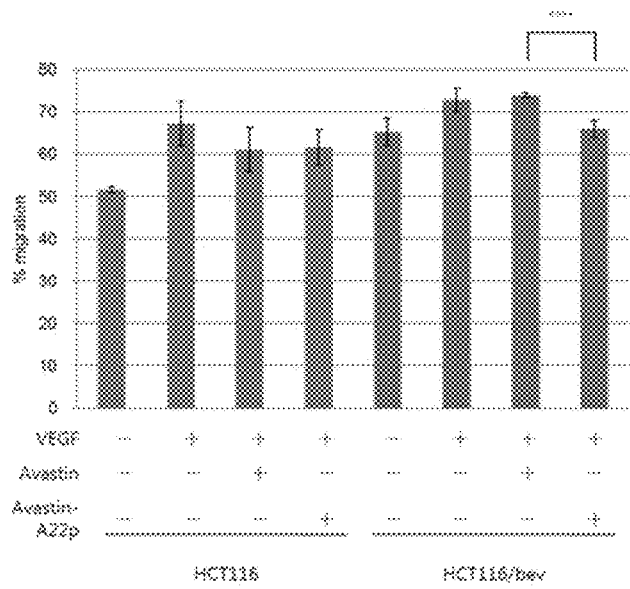

Results are shown in FIG. 8.

As shown in FIG. 8, the migration of HCT116 cells was increased from 51.7% to 67.4% by VEGF, whereas it was reduced to the same level of 61.2% and 61.7% for Avastin and Avastin-A22p treatment, respectively. On the contrary, as for HCT116/bev cells, the migration of HCT116/bev cells was 65.3% even in the group treated with no VEGF, indicating that HCT116/bev cells were more aggressive than HCT116 cells, while the migration of HCT116/bev cells was increased to 72.9% by VEGF treatment. It was observed that such migration was 74.1% by Avastin treatment which indicated no difference in migration, while such migration was 66.2% by Avastin-A22p treatment which indicated that the migration was suppressed to the same level as in the group treated with no VEGF.

The results that Avastin-adapted cell lines, HCT116/bev, showed increased migration in comparison with their parent cells, HCT116, regardless of the addition of VEGF-A indicated that the migration of HCT116/bev was increased dependent on not only VEGF-A but also other growth factors. The Avastin treatment did not suppress the migration, whereas the Avastin-A22p treatment reduced migration to the same level as in the treatment without VEGF-A. This means that Avastin-A22p inhibits signalings by other growth factors as well as VEGF-A, indicating that Avastin-A22p may contribute to overcoming of Avastin resistance. In addition, this result suggests that Avastin-A22p can promote anticancer effects and lower the possibility of resistance occurrence by inhibiting not only VEGF-A signaling but also other signaling procedures.

Example 7: Evaluation on PDGF Signaling Inhibition by Avastin-A22p

NRP1 acts as a co-receptor for PDGF receptor to enhance signaling by PDGF. It is known that the binding of PDGF to a receptor thereof in cancer cells increases the phosphorylation of p130cas protein and promotes the migration and invasion of cancer cells. The present inventors investigated whether A22p fused to Avastin inhibits PDGF signaling by binding to NRP1.

U87MG cells (obtained from ATCC) were treated with 25 μg/ml Avastin or Avastin-A22p and, after 30 min, treated with 50 ng/ml PDGF. After 5 min, proteins were extracted, and then the comparison of p130cas phosphorylation was carried out using anti-phospho-p130 antibody and anti-p130cas antibody.

Figure 9A:
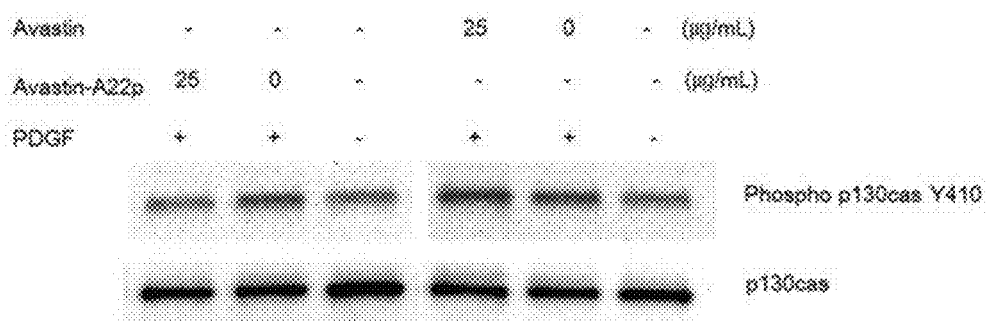
FIGS. 9A and 9B show the results of confirming the protein phosphorylation of p130cas when U87MG cells were treated with 25 μg/ml Avastin or Avastin-A22p and, after 30 min, treated with 50 ng/ml PDGF, in order to investigate whether Avastin-A22p inhibits PDGE-mediated signaling (FIG. 9A: western blotting results, FIG. 9B: graph to quantify western blotting results, A22p+P: Avastin-A22p 25 ug/ml+PDGF 50 ng/ml, P: PDGF 50 ng/ml, C: control, A+P: Avastin 25 ug/ml+PDGF 50 ng/ml).
Figure 9B:
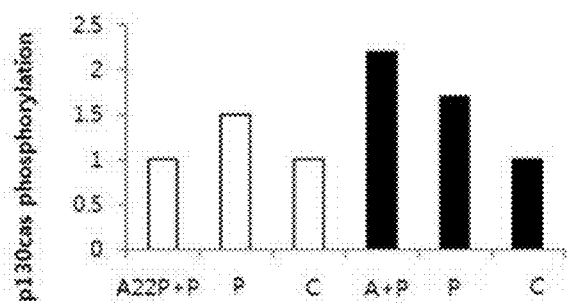

Results are shown in FIG. 9.

As shown in FIG. 9, it was verified that p130cas phosphorylation was increased by PDGF, and Avastin treatment resulted in no difference, but the phosphorylation in the Avastin-A22p treatment group was suppressed to the level in the vehicle.

This result means that Avastin-A22p removes VEGF-A, and also suppresses PDGF signaling by binding to NRP1, and that Avastin-A22p can increase anticancer effects by suppressing migration and invasion by PDGF.

Example 8: Preparation of Avastin Variant-Tissue-Penetrating Peptide (TPP) Fusion Protein In order to investigate whether a fusion protein, in which a tissue-penetrating peptide (TPP) was fused to a variant containing a frequently modified sequence in other antibody medicines while retaining its characteristics, it was attempted that a tissue-penetrating peptide (TPP) capable of binding to both neuropilin 1 (NRP1) and neuropilin 2 was fused to the C-terminus of the Avastin variant peptide (hereinafter, referred to as "Avastin(V)) with modifications of 362nd and 364th amino acids in the Avastin's amino acid sequence.

Specifically, a fusion protein in which TPP (A22p) having the amino acid sequence of SEQ ID: 2 was fused to C-terminus of Avastin (V), and a cell line producing the fusion protein were prepared, respectively. Selection marker DHFR genes were inserted into pcDNA3.1(−) vectors and heavy and light chains of Avastin(V)-A22p were cloned by restriction enzymes NotI and BamHI. A plasmid encoding the protein formed by fusion of each of the constructed antibody heavy constant regions and a peptide binding to NRP1 and a plasmid encoding a light chain protein were expressed for protein in CHO DG44 cells using Neon™ electroporesis. In T25 flask, $3 \times 10^6$ cells transfected with plasmid were inoculated, and incubated at 37° C. Stable cells were secured using the selection marker, and then cultured in a floating state in serum-free SFM4CHO (Hyclone) for 7 days under conditions of 100 rpm, 37° C., pH 7.2, 50% $DO_2$ in a bioreactor. The supernatant was separated from the cells by centrifugation, and sterilized by a 0.22-um filter.

The culture of Avastin(V)-A22p was collected, and proteins were respectively purified while referring to a standard protocol. For the purification column, the protein A resin (MabselectSure resin, GE healthcare) was packed to 20 mL in the XK16/20 column (MabselectSure resin, GE healthcare), to which a linear speed of 200 cm/h was applied. 1 L of antibody was applied to the protein A column, and the column was washed with a 15-fold column volume of PBS (pH 7.4, 137 mM NaCl, 2.7 mM KCl, 10 mM $Na_2HPO_4$, 2 mM $KH_2PO_4$). The antibody was eluted with 100 mL of 0.1 M glycine buffer at pH 3.0. The proteins were collected between 10 mAU and 10 mAU in the UV absorbance at 280 nm, and 60 mL of the proteins were neutralized to pH 7.0 using 0.7 mL of 1 M Tris buffer. The antibody fractions were filtered by a 0.2 μm-filter (Millipore), and then concentrated using an amicon (30 MWCO) concentrator (Millipore) at 3,500 rpm for 10 min, followed by exchange with PBS (pH 7.4) buffer containing 10% glycerol. The purified fusion protein formed by fusion of the purified the antibody heavy chain constant region and the selected peptide specifically binding to NRP1 was analyzed on SDS-PAGE in reduction and non-reduction conditions.

Figure 10:
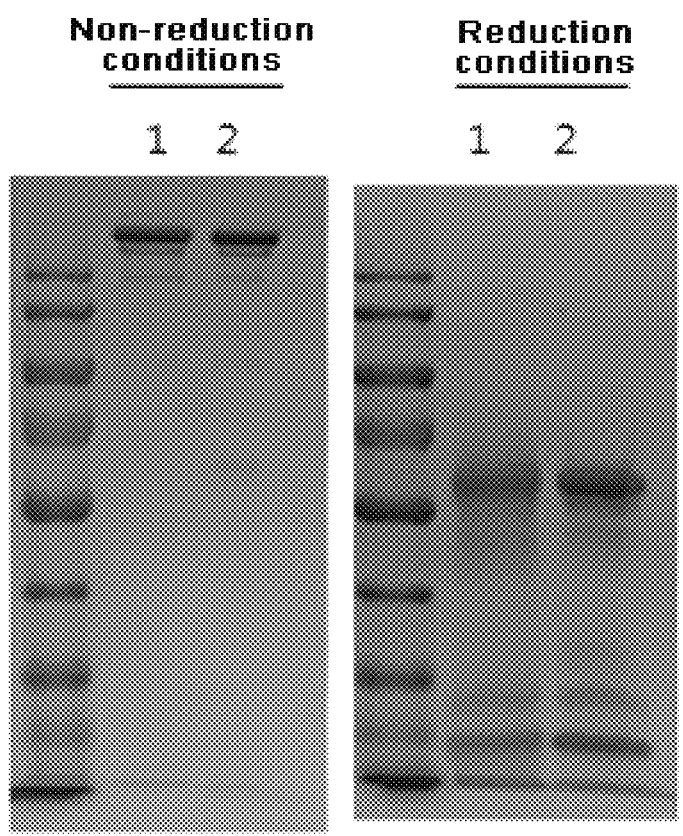
FIG. 10 shows SDS-PAGE results of confirming a fusion protein formed by fusion of a tumor-penetrating peptide and an anti-vascular endothelial growth factor (Lane 1: Avastin (V)-A22p, Lane 2: Avastin-A22p).

Respective proteins were purified from the cultures collected from the cell lines expressing Avastin(V)-A22p and Avastin-A22p, and isolated by SDS-PAGE. FIG. 10 confirmed that Avastin(V)-A22p successfully formed antibody, and has a similar molecular weight to Avastin-A22p.

In order to investigate the purity of Avastin(V)-A22p purified protein, high performance liquid chromatography (HPLC) assay was performed. Agilent 1200 (Agilent) was used, and a size exclusion column (Biosuite 250, Waters) was used.

Specifically, a buffer solution (pH 6.2) containing 0.2 M potassium phosphate and 0.25 M potassium chloride was used as a mobile phase, and allowed to flow down at a flow rate of 0.35 ml/min for 20 min. The size of the protein was checked according to the retention time, and the purity thereof was checked according to the area and height.

Figure 11A:
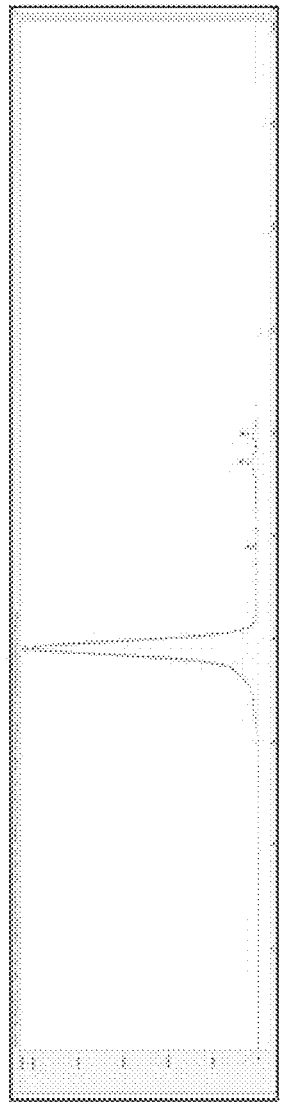
FIGS. 11A and 11B show SE-HPLC results of confirming a fusion protein formed by fusion of a tumor-penetrating peptide and an anti-vascular endothelial growth factor (FIG. 11A: Avastin(V)-A22p, FIG. 11B: Avastin-A22p).
Figure 11B:
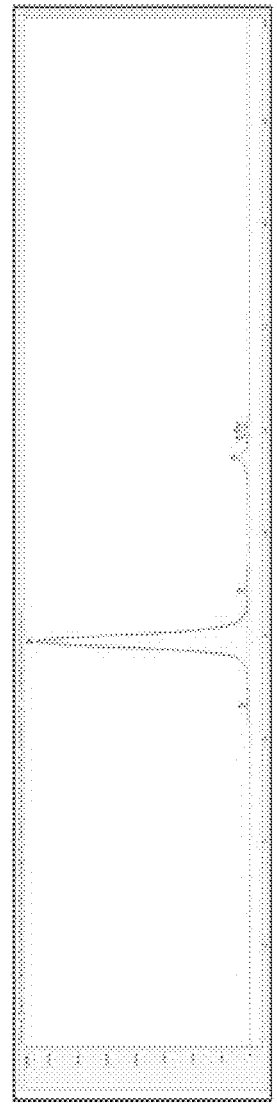

In FIG. 11, the purity of Avastin(V)-A22p was analyzed using SE-HPLC. It was verified that the purity of Avastin (V)-A22p was 97% or higher (FIG. 11A), which was the same as the purity of Avastin-A22p (FIG. 11B).

The present inventors, hereinafter, prepared an Avastin (V)-A22p fusion protein in which A22p as a TPP having the amino acid sequence represented by SEQ ID NO: 2 was fused to Avastin(V), and evaluated activity thereof.

Example 9: Binding Ability of Avastin(V)-Tissue-Penetrating Peptide (TPP) Fusion Protein to NRP1 and VEGF In order to evaluate whether the N-terminus of the fusion protein Avastin(V)-A22p as prepared in Example 8 may bind to VEGF in the same manner as Avastin while its C-terminus may bind to NRP1 to thus dually block the associated signaling, the binding of Avastin(V)-A22p with NRP1 and VEGF was respectively evaluated.

The binding ability of the purified Avastin(V)-A22p to Neuropilin 1-b1b2 domain was investigated in enzyme-linked immunosorbant assay (ELIA). Avastin-A22p was used as a positive control. The target molecule Neuropilin 1-b1b2 domain (273-586) was reacted at 1 μg per well in the 96-well Maxibinding Immuno plate (SPL Life sciences., Korea) for 2 h at 37° C., and then washed with 0.1% PBST (0.1% Tween20, pH 7.4, 137 mM NaCl, 2.7 mM KCl, 10 mM $Na_2HPO_4$, 2 mM $KH_2PO_4$) for 1 min three times. After reaction with 0.1% PBST containing 5% skim milk for 1 h, the reaction product was washed with 0.1% PBST for 1 min three times. Avastin(V)-A22p, as experimental groups, was diluted with 0.1% PBST to 50 nM, 25 nM, and 12.5 nM, and the solutions were then treated at 37r for 1 h for each different concentrations, and washed with 0.1% PBST for 1 min three times. HRP-conjugated anti-kappa light chain antibody (Horseradish peroxidase-conjugated anti-human kappa light chain mAb, SIGMA-ALDRICH Co., USA) was 100,000-fold diluted with 0.1% PBST containing 5% skim milk, followed by treatment at 37r for 30 min. Thereafter, the reaction product was washed with 0.1% PBST for 1 min five times. For color development, the resultant product was treated with the TMB HRP colorimetric substrate (Surmodics co., USA), followed by reaction at room temperature for 10 min, treatment with the same volume of 1 N HCl (stop buffer), and then absorbance measurement at 450 nm. The binding ability of the expressed and purified Avastin(V)-A22p to Neuropilin 1-b1b2 domain was confirmed through the obtained ELISA results.

The binding ability of the purified Avastin(V)-A22p to Recombinant human VEGF 165 (R&D systems co. China) was investigated in ELISA. Avastin-A22p was used as a positive control. The target molecule Recombinant human VEGF 165 was reacted at 0.2 μg per well in the 96-well Maxibinding Immuno plate for 2 h at 37° C., and then washed with 0.1 PBST for 1 min three times. After reaction with 0.1% PBST containing 5% skim milk for 1 h, the reaction product was washed with 0.1% PBST for 1 min three times. Avastin(V)-A22p, as experimental groups, was diluted with 0.1% PBST to 6.25 nM, 3.12 nM, and 1.56 nM, and the solutions were then treated at 37r for 1 h for each different concentrations, and washed with 0.1% PBST for 1 min three times. HRP-conjugated anti-kappa light chain antibody was 100,000-fold diluted with 0.1% PBST containing 5% skim milk, followed by treatment at 37° C. for 30 min. Thereafter, the reaction product was washed with 0.1% PBST for 1 min five times. For color development, the resultant product was treated with the TMB HRP colorimetric substrate, followed by reaction at room temperature for 10 min, treatment with the same volume of 1 N HCl, and then absorbance measurement at 450 nm. The binding ability of the expressed and purified Avastin(V)-A22p to Recombinant human VEGF 165 was confirmed through the obtained ELISA results.

Results are shown in FIG. 12.

Figure 12A:
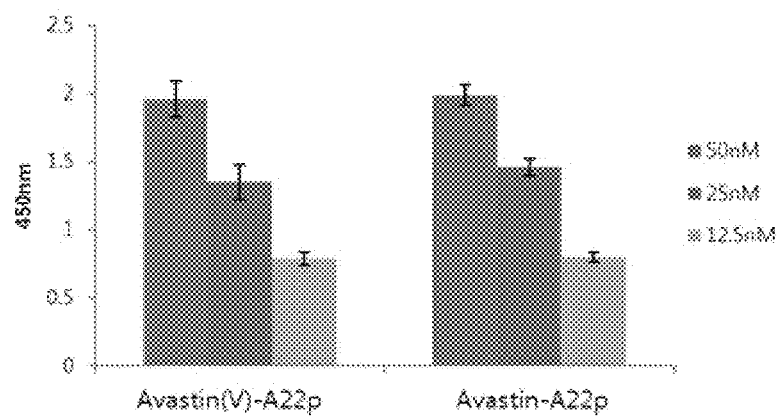
FIGS. 12A and 12B show the results of evaluating the binding strength of Avastin(V)-A22p with NRP1 or VEGF, in comparison with Avastin-A22p (FIG. 12A: binding strength with NRP1, FIG. 12B: binding strength with VEGF).
Figure 12B:
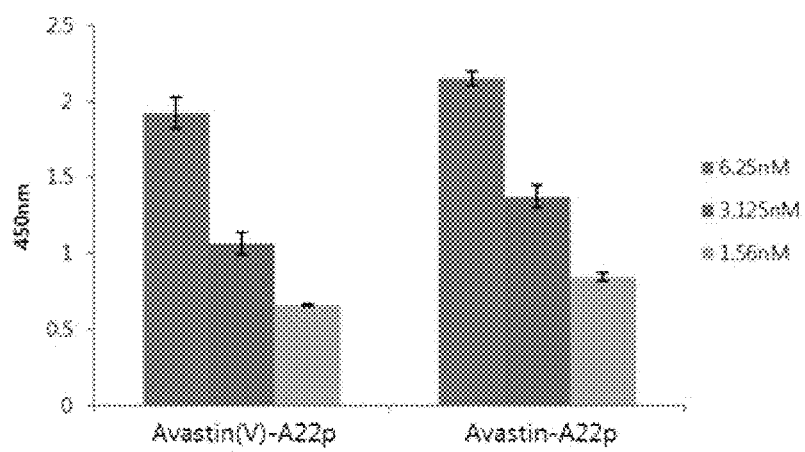

As shown in FIG. 12, it was confirmed that Avastin(V)-A22p bound to NRP1 at the same level as in Avastin-A22p used as a control (FIG. 12A), and also bound to VEGF at the same level as Avastin-A22p (FIG. 12B).

INDUSTRIAL APPLICABILITY

The pharmaceutical composition containing, as an active ingredient, a fusion protein formed by fusion of a tissue-penetrating peptide and an anti-angiogenic agent, for treating cancer or an angiogenesis-related disease may improve the tumor penetration of the anti-angiogenic agent and exert a cancer targeting effect, thereby exhibiting an excellent therapeutic effect with even a small dose and thus reducing side effects of the anti-angiogenic agent, while exhibiting an excellent therapeutic effect even on cancer or an angiogenesis-related disease having resistance to the anti-angiogenic agent by binding to an angiogenesis growth factor and NRP1 at the same time. Therefore, the present invention is highly industrially applicable.

The invention claimed is:

1. A composition comprising, as an active ingredient, a fusion protein obtained by fusion of a tumor-penetrating peptide and an anti-vascular endothelial growth factor (anti-VEGF) agent, wherein the tumor-penetrating peptide comprises the amino acid of SEQ ID NO: 1 or SEQ ID NO: 2, and the anti-VEGF agent is selected from the group consisting of ranibizumab, bevacizumab, aflibercept, conbercept, r84, CT01, DOM15-10-11, DOM15-26-593, PRS-050, CT-322, ESBA903, and EPI-0030.

2. The composition of claim 1, wherein the tumor-penetrating peptide binds to both neuropilin 1 (NRP1) and neuropilin 2 (NRP2).

3. The composition of claim 1, wherein the tumor-penetrating peptide and the anti-VEGF agent are fused via a linker.

4. The composition of claim 3, wherein the linker comprises an amino acid sequence represented by SEQ ID NO: 8.

5. The composition of claim 1, wherein the fusion protein comprises a heavy chain defined by any one amino acid sequence selected from the group consisting of SEQ ID NO: 9 and SEQ ID NO: 12, and a light chain defined by the amino acid sequence of SEQ ID NO: 11.

6. A method for treating cancer or an angiogenesis-related disease in a subject in need thereof, the method comprising administering an effective amount of a composition to a subject in need thereof, the composition comprising, as an active ingredient, a fusion protein formed by fusion of a tumor-penetrating peptide and an anti-vascular endothelial growth factor (anti-VEGF) agent, wherein the tumor-penetrating peptide comprises the amino acid of SEQ ID NO: 1 or SEQ ID NO: 2, and the anti-VEGF agent is selected from the group consisting of ranibizumab, bevacizumab, aflibercept, conbercept, r84, CT01, DOM15-10-11, DOM15-26-593, PRS-050, CT-322, ESBA903, and EPI-0030.

7. The method of claim 6, wherein the cancer or angiogenesis-related disease is resistant or non-responsive to the anti-VEGF agent.

8. The method of claim 6, wherein the angiogenesis-related disease is selected from the group consisting of rheumatoid arthritis, psoriasis, inflammation, endometriosis, and angioma.

9. The method of claim 6, wherein the cancer is selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, perianal cancer, esophageal cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, colorectal cancer, endometrial or uterine cancer, salivary gland tumor, kidney cancer, liver cancer, prostate cancer, vulvar cancer, thyroid cancer, and head or neck cancer.

10. A method for inhibiting metastasis in a subject in need thereof, the method comprising administering an effective amount of a composition to a subject in need thereof, the composition comprising, as an active ingredient, a fusion protein formed by fusion of a tumor-penetrating peptide and an anti-vascular endothelial growth factor (anti-VEGF) agent, wherein the tumor-penetrating peptide comprises the amino acid of SEQ ID NO: 1 or SEQ ID NO: 2, and the anti-VEGF agent is selected from the group consisting of ranibizumab, bevacizumab, aflibercept, conbercept, r84, CT01, DOM15-10-11, DOM15-26-593, PRS-050, CT-322, ESBA903, and EPI-0030.

* * * * *

SEQUENCE LISTING

```
<160> NUMBER OF SEQ ID NOS: 13

<210> SEQ ID NO 1
<211> LENGTH: 22
<212> TYPE: PRT
<213> ORGANISM: Artificial Sequence
<220> FEATURE:
<223> OTHER INFORMATION: TPP(tumor penetrating peptide)#1

<400> SEQUENCE: 1

His Thr Pro Gly Asn Ser Asn Lys Trp Lys His Leu Gln Glu Asn Lys
1               5                   10                  15

Lys Gly Arg Asn Arg Arg
            20

<210> SEQ ID NO 2
<211> LENGTH: 22
<212> TYPE: PRT
<213> ORGANISM: Artificial Sequence
<220> FEATURE:
<223> OTHER INFORMATION: TPP(tumor penetrating peptide)#2

<400> SEQUENCE: 2

His Thr Pro Gly Asn Ser Asn Lys Trp Lys His Leu Gln Glu Asn Lys
1               5                   10                  15
```

```
Lys Gly Arg Pro Arg Arg
            20

<210> SEQ ID NO 3
<211> LENGTH: 22
<212> TYPE: PRT
<213> ORGANISM: Artificial Sequence
<220> FEATURE:
<223> OTHER INFORMATION: TPP(tumor penetrating peptide)#3

<400> SEQUENCE: 3

Arg Glu Ala Pro Gly Ala Pro Arg Ser Pro Glu Pro Gln Asp Gln Lys
1               5                   10                  15

Lys Pro Arg Asn Arg Arg
            20

<210> SEQ ID NO 4
<211> LENGTH: 22
<212> TYPE: PRT
<213> ORGANISM: Artificial Sequence
<220> FEATURE:
<223> OTHER INFORMATION: TPP(tumor penetrating peptide)#4

<400> SEQUENCE: 4

Arg Glu Ala Pro Gly Ala Pro Arg Ser Pro Glu Pro Gln Asp Gln Lys
1               5                   10                  15

Lys Pro Arg Pro Arg Arg
            20

<210> SEQ ID NO 5
<211> LENGTH: 18
<212> TYPE: PRT
<213> ORGANISM: Artificial Sequence
<220> FEATURE:
<223> OTHER INFORMATION: TPP(tumor penetrating peptide)#5

<400> SEQUENCE: 5

His Thr Pro Gly Asn Ser Asn Gln Phe Val Leu Thr Ser Thr Arg Pro
1               5                   10                  15

Pro Arg

<210> SEQ ID NO 6
<211> LENGTH: 11
<212> TYPE: PRT
<213> ORGANISM: Artificial Sequence
<220> FEATURE:
<223> OTHER INFORMATION: TPP(tumor penetrating peptide)#6

<400> SEQUENCE: 6

His Thr Pro Gly Ile Ala Thr Arg Thr Pro Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: TPP(tumor penetrating peptide)#7

<400> SEQUENCE: 7

His Thr Pro Gly Asn Ser Lys Pro Thr Arg Thr Pro Arg Arg
1               5                   10

<210> SEQ ID NO 8
```

```
<211> LENGTH: 15
<212> TYPE: PRT
<213> ORGANISM: Artificial Sequence
<220> FEATURE:
<223> OTHER INFORMATION: Linker

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 490
<212> TYPE: PRT
<213> ORGANISM: Artificial Sequence
<220> FEATURE:
<223> OTHER INFORMATION: Avastin-HC-A22p

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
```

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
            325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
            355                 360                 365

Val Glu Trp Glu Ser Asn Gly Gln Pro Glu Asn Asn Tyr Lys Thr Thr
370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
            405                 410                 415

Val Met His Glu Ala Leu His Asn His Tyr Thr Gln Lys Ser Leu Ser
            420                 425                 430

Leu Ser Pro Gly Lys Gly Gly Gly Ser Gly Gly Gly Ser Gly
            435                 440                 445

Gly Gly Ser His Thr Pro Gly Asn Ser Asn Lys Trp Lys His Leu
450                 455                 460

Gln Glu Asn Lys Lys Gly Arg Pro Arg Arg
465                 470                 475                 480

485                 490

<210> SEQ ID NO 10
<211> LENGTH: 482
<212> TYPE: PRT
<213> ORGANISM: Artificial Sequence
<220> FEATURE:
<223> OTHER INFORMATION: Avastin-HC-TPP11

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

```
                180             185                 190
Thr Val Pro Ser Ser Leu Gly Thr Gln Thr Tyr Ile Cys Asn Val
            195                 200             205
Asn His Lys Pro Ser Asn Thr Lys Val Asp Lys Val Glu Pro Lys
            210                 215             220
Ser Cys Asp Lys Thr His Thr Cys Pro Pro Cys Pro Ala Pro Glu Leu
225             230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
            290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
            435                 440                 445
Leu Ser Pro Gly Lys Gly Gly Gly Gly Ser Gly Gly Gly Gly Ser Gly
            450                 455                 460
Gly Gly Gly Ser His Thr Pro Gly Asn Ser Lys Pro Thr Arg Thr Pro
465                 470                 475                 480
Arg Arg

<210> SEQ ID NO 11
<211> LENGTH: 214
<212> TYPE: PRT
<213> ORGANISM: Artificial Sequence
<220> FEATURE:
<223> OTHER INFORMATION: Avastin-LC

<400> SEQUENCE: 11

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 490
<212> TYPE: PRT
<213> ORGANISM: Artificial Sequence
<220> FEATURE:
<223> OTHER INFORMATION: Avastin(V)-HC-A22p

<400> SEQUENCE: 12

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Gly Ser Gly
    450                 455                 460

Gly Gly Gly Ser His Thr Pro Gly Asn Ser Asn Lys Trp Lys His Leu
465                 470                 475                 480

Gln Glu Asn Lys Lys Gly Arg Pro Arg Arg
                485                 490

<210> SEQ ID NO 13
<211> LENGTH: 453
<212> TYPE: PRT
<213> ORGANISM: Artificial Sequence
<220> FEATURE:
<223> OTHER INFORMATION: Avastin-HC

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450
```